US012227738B2

(12) United States Patent
Peršič Debenjak et al.

(10) Patent No.: US 12,227,738 B2
(45) Date of Patent: Feb. 18, 2025

(54) METHOD OF SINGLE-STRANDED RNA PURIFICATION

(71) Applicant: Sartorius BIA Separations d.o.o., Ajdovscina (SI)

(72) Inventors: Špela Peršič Debenjak, Dobrovo (SI); Urh Černigoj, Ajdovscina (SI); Darko Dolenc, Vrhnika (SI); Peter S. Gagnon, Las Vegas, NV (US)

(73) Assignee: Sartorius BIA Separations d.o.o., Ajdovscina (SI)

( * ) Notice: Subject to any disclaimer, the term of this patent is extended or adjusted under 35 U.S.C. 154(b) by 0 days.

(21) Appl. No.: 17/917,084

(22) PCT Filed: Apr. 16, 2021

(86) PCT No.: PCT/EP2021/059903
§ 371 (c)(1),
(2) Date: Oct. 5, 2022

(87) PCT Pub. No.: WO2021/209595
PCT Pub. Date: Oct. 21, 2021

(65) Prior Publication Data
US 2023/0151351 A1    May 18, 2023

(30) Foreign Application Priority Data

Apr. 17, 2020  (EP) .................................... 20170205

(51) Int. Cl.
*C12N 15/10*    (2006.01)
(52) U.S. Cl.
CPC ................. *C12N 15/101* (2013.01)
(58) Field of Classification Search
CPC .......................... C12N 15/01; C12N 15/1006

USPC ........................................................ 536/25.4
See application file for complete search history.

(56) References Cited

FOREIGN PATENT DOCUMENTS

| EP | 0270017 A2 * | 6/1988 | ......... C12N 15/1006 |
| EP | 1693453 A1 * | 8/2006 | ......... C12N 15/1006 |
| WO | WO 2009/020609 A2 * | 2/2009 | ............. C12N 15/10 |
| WO | 2017-182524 A1 | 10/2017 | |

OTHER PUBLICATIONS

Baiersdörfer et al., "A Facile Method for the Removal of dsRNA Contaminant from In Vitro-Transcribed mRNA", Molecular Therapy: Nucleic Acids, vol. 15, p. 26-35, (Apr. 2019).
Pe'ery et al., "Synthesis and Purification of Single-Stranded RNA for Use in Experiments with PKR and in Cell-Free Translation Systems", Methods: A Companion to Methods Enzymology, vol. 11, p. 371-381 (1997).
International Search Report for corresponding Patent Application No. PCT/EP2021/059903 dated Oct. 8, 2021.

* cited by examiner

*Primary Examiner* — Ganapathy Krishnan
(74) *Attorney, Agent, or Firm* — Christensen, Fonder, Dardi PLLC; Diane E. Bennett; Peter S. Dardi

(57) ABSTRACT

A method of single-stranded RNA purification comprising the steps
applying a sample containing single-stranded RNA to a solid phase bearing dominantly or exclusively primary amino groups on its surface, at a pH value sufficient to bind at least predominantly the single-stranded RNA,
eluting the single-stranded RNA from the surface of the solid phase by exposing the surface of the solid phase to increasing pH.

20 Claims, 5 Drawing Sheets

METHOD OF SINGLE-STRANDED RNA PURIFICATION

CROSS REFERENCE TO RELATED APPLICATIONS

This application is a National Stage filing of PCT Application No. PCT/EP2021/059903 filed Apr. 16, 2021, entitled "A Method of Single-Stranded RNA Purification", which claims priority to European Patent Application No. 20170205.7, filed Apr. 17, 2020.

The invention pertains to a method for removing double-stranded RNA from an essentially aqueous mixture of double-stranded RNA and single-stranded RNA.

BACKGROUND

Synthesis of messenger RNA (mRNA) for gene therapy applications yields preparations that contain undesired subpopulations of double-stranded (ds) RNA in addition to the desired single-stranded (ss) RNA. These dsRNA species form post-synthesis by intrachain interaction of complementary sequences within the base-strand. Formation of dsRNA sequences can also occur by pairing with complementary sequences among neighboring ssRNA molecules, thereby creating non-specific interchain dimers and higher order multimers that may also contain intrachain ds sequences. Double-stranded RNA triggers an unwanted and potentially lethal immune response when injected into a subject, making its removal a particular object of purification.

Methods for reducing the content of dsRNA from mRNA preparations are known. Levels of dsRNA contamination can be reduced by affinity-adsorption chromatography on cellulose based chromatography media [1-3]. The precise mechanism of adsorption has not been defined but dsRNA binds under certain conditions while ssRNA flows through. The method is simple and effective at laboratory scale but it is burdened by very low capacity. Low capacity corresponds with large column volumes at manufacturing scale, which require large buffer volumes, large manufacturing areas, and extended process time that depresses productivity of the manufacturing facility. The method also causes dilution of the processed ssRNA, corresponding to an increase of product volume that burdens follow-on purification steps.

Levels of dsRNA may alternatively be reduced by reverse phase chromatography (RPC) using a styrene-divinyl-benzene (SDVB) solid phase [4-7]. RPC employs toxic flammable organic solvents that require extremely expensive specialized equipment at industrial scale to miti-gate the risk of fire and explosion. RPC also imposes the further burden of safety issues as they pertain to organic solvent toxicity in the work environment and to hazardous waste disposal issues. In addition to the solvent issues, RPC separations often bear the further burden of requiring elevated temperature to obtain the best results.

Anion exchange chromatography has shown utility for purification of small mRNA (<1000 bases) [8]. Anion exchange media evaluated to date include so-called strong anion exchangers, referring to quaternary amine (QA) anion exchangers. So-called weak anion exchangers have also been evaluated, in particular diethylaminoethyl (DEAE) anion exchangers employing a tertiary amine ligand.

Anion exchange chromatography has shown limited utility for removal of DNA and protein contaminants from large mRNA (1,000-10,000 bases) but only at elevated operating temperatures [9]. Elevating the temperature to 65° C. enables elution of large mRNA in a sodium chloride gradient. However, high temperature operation imposes a compound logistical burden since the buffers, samples, and column must all be pre-equilibrated to and maintained precisely at the specified operating temperature for the entire duration of the process, and reproducibly across all batches for the manufacturing life of the product, potentially for years.

Proteins are known to be eluted from anion exchangers by descending pH gradients because proteins become more electropositive and less electronegative with decreasing pH, with the eventual effect suspending their association with the anion exchanger. This approach does not and cannot work with RNA because its charge characteristics remain uniform from about pH 2.6 to pH 13.0. Elution of biomolecules from anion exchangers by increasing pH is known not to work because it causes them to bind more strongly. Proteins can be eluted from cation exchangers by increasing pH gradients but the method has no utility for separation of dsRNA from ssRNA because neither binds to cation exchangers.

SUMMARY

A novel method has been developed for removal of dsRNA from mixed preparations with ssRNA that represents an improvement over known methods. It is pertinent to mRNA of all sizes but particularly to large and very-large mRNA, such as in the size range of 1,000-25,000 bases. The method enables separation of ssRNA and dsRNA bound to a primary amino solid phase by means of an ascending pH gradient. ssRNA elutes at higher pH than dsRNA. The method also permits fractionation of ssRNA according to its size.

According to the invention a method of single-stranded RNA purification is claimed comprising the steps of:
  applying a sample containing single-stranded RNA to a solid phase bearing dominantly or exclusively primary amino groups on its surface, at a pH value sufficient to bind at least predominantly the single-stranded RNA,
  eluting the single-stranded RNA from the surface of the solid phase by exposing the surface of the solid phase to increasing pH.

In an embodiment of the method of the invention after applying the sample and prior to eluting of the single-stranded RNA at least one step of washing of the solid phase with a washing buffer having a higher ionic strength compared to an elution buffer used for eluting of the single-stranded RNA can be provided.

In another embodiment of the method of the invention at least one step of washing can be provided to reduce the higher ionic strength.

In a further embodiment of the method of the invention after applying the sample and prior to eluting of the single-stranded RNA at least one washing step may be provided with a washing buffer having an increased pH which keeps single-stranded RNA adsorbed to the solid phase and desorbs remaining double-stranded RNA.

The washing steps can be combined as two subsequent washing steps after applying the sample to the solid phase.

In yet another embodiment of the method of the invention the ionic strength of the washing buffer can be selected in the range of 0.5 M to 12 M, or 1.0 M to 10 M, or 2.0 M to 8.0 M, or 4.0 M to 6.0 M higher as compared to the ionic strength of buffer required to elute the single-stranded RNA. If NaCl is used, ionic strength corresponds to molarity of the solution. For example, the ionic strength of the washing buffer can be 2.5 M when the corresponding ionic strength at which ssRNA elutes is less than 2.0 M. In another example, the ionic strength of the washing buffer can be 1.0 M when the ionic strength at which ssRNA elutes is 0.5 M.

Typically, the molarity of the washing buffer is in a range of 0.51 M to 12.0 M whereas the molarity at which ssRNA elutes is in a range of 0.01 M to 0.5 M.

In still another embodiment of the method of the invention the ionic strength of the washing buffer may be adjusted with a concentration of a chaotropic salt, in particular selected from the group consisting of guanidinium salts, thiocyanates, perchlorates and combinations thereof. In a further embodiment of the method of the invention eluting of the single-stranded RNA from the surface of the solid phase can occur by means of an elution buffer having a pH in a pH range of pH 7.5 to pH 12.0, or pH 8.0 to pH 11.5, or pH 8.5 to pH 11, or pH 9.0 to pH 10.5.

In still a further embodiment of the method of the invention applying the sample to the solid phase may occur at a pH value of less than about pH 8.5.

In yet a further embodiment of the method of the invention a chelating agent can be present in the essentially aqueous mixture, in an environment of the surface of the solid phase prior to the contacting of the aqueous mixture, in a buffer for eluting the single-stranded RNA from the surface of the solid phase and/or in a separate buffer employed between the steps of applying the sample to the solid phase and/or eluting the single-stranded RNA from the surface of the solid phase.

In another embodiment of the method of the invention the chelating agents can be independently selected from the group consisting of ethylenediaminetetraacetic acid (EDTA), a salt of citric acid, phosphoric acid, or ethylene glycol-bis(2-aminoethylether)-N,N,N',N'-tetraacetic acid (EGTA), tris(2-aminoethyl)-iamine (TREN), and a mixture thereof.

Typically, the single-stranded RNA is of size in the range of 1,000 bases to 25,000 bases. Subject matter of the present invention is also the use of a solid phase comprising dominantly or exclusively primary amino groups on its surface for single-stranded RNA purification. In particular single-stranded RNA can purified or separated from double-stranded RNA by means of an increasing pH.

The surprising nature of the method is highlighted by the fact that it teaches against the prior art at multiple levels. The published art teaches that separation of large ssRNA from large dsRNA with strong (QA) and weak (DEAE) anion exchangers at ambient temperature is impossible.

This highlights a second surprising feature of the invention, that elution of any biomolecule species from any anion exchanger by means of increasing pH is considered impossible. It violates a foundation principle known in the art for decades. That principle is that acidic solutes (net negative charge) bind strong anion exchangers more strongly with increasing pH. On the infrequent occasions that anion exchangers are eluted with pH gradients, they are eluted exclusively with descending pH gradients: opposite to the method of the invention.

The invention embodies a third surprising feature without precedent in the art. Preliminary data document that elution of ssRNA from a primary amino solid phase by means of a pH gradient sorts ssRNA species according to size, with higher pH values being required to elute larger ssRNA species. Remarkably, size discrimination among dsRNA species is comparatively poor.

The invention also embodies a fourth surprising feature without precedent in the art. Experimental data show that dsRNA does not interact with a primary amino solid phase in the same way that ssRNA behaves with the same surface. This is unexpected because ssRNA and dsRNA in a given in vitro transcription mixture are compositionally identical, having the same number of nucleotide bases in the same sequence. Remarkably, a wide variety of salts are able to displace the majority of dsRNA from a primary amino solid phase without eluting the desired ssRNA. Even more remarkably, ssRNA is not eluted even by extremely high concentrations of known aggressive chaotropic salts.

No theory has yet been developed to account for the paradoxical behavior of a primary amino solid phase eluted with an ascending pH gradient; why it violates expectations based on traditional anion exchangers, how it separates dsRNA from ssRNA, or how it achieves size fractionation of ssRNA.

Beyond simply displacing dsRNA in advance of eluting ssRNA, high-salt washes offer a unique opportunity to dissociate otherwise-stable complexes between ssRNA and contaminants such as proteins and DNA. This provides a solution to a major challenge in the field that is only beginning to be recognized. Nucleic acids frequently exist in stable complexes with contaminants. Some of those complexes elute under the same or nearly the same conditions as pure nucleic acid. These complexes accordingly represent Trojan Horses that smuggle contaminants into what should be the pure ssRNA elution fraction, even though the properties of the independent contaminants should preclude that possibility. Dissociating high-salt washes offer the possibility to suspend that contamination pathway. The complex-dissociative potential of this approach is enhanced with chaotropic salts such as guanidine that embody stronger dissociative potential than neutral salts such as NaCl. Complex-dissociative potential can be further enhanced by the presence of chelating agents.

The inability of contaminating dsRNA to bind to a primary amino solid phase in high-salt chemical environments also enables a workflow simplification that rivals a technique known in the art as affinity chromatography. Affinity chromatography is a technique in which a biospecific ligand such as an antibody is covalently affixed to a solid phase. When a contaminated sample bearing the target of that antibody is applied to the solid phase, only the target molecule is captured while contaminants are eliminated by flowing through the column. After washing the column to rinse away trace levels of undesired species, the target molecule is eluted in a single highly purified fraction. In the present case, sample containing dsRNA and ssRNA is loaded in high salt at neutral pH. The majority of the dsRNA flows through the solid phase. Highly purified ssRNA is eluted in a concentrated fraction by an increase in pH.

It will be recognized by persons of experience in the art this workflow simplification represents a minor procedural variation employing the same principal employed in the basic configuration of the invention, that principal being that dsRNA is unbound by the primary amino solid phase in the presence of high concentrations of salt.

A final surprising feature of the invention is that the elution behavior of contaminants differing in composition from RNA elute similarly to dsRNA but differently from ssRNA. Such contaminants include proteins and DNA, both of which elute earlier than ssRNA in pH gradients.

The majority of them are also removed by salts applied to the solid phase in advance of separating their trace residues from ssRNA by means of an ascending pH gradient.

General Description of the Invention

In a general aspect, the invention is a solid phase extraction method for removal of double-stranded messenger RNA (dsRNA) from a preparation containing a mixture of dsRNA and single-stranded messenger RNA (ssRNA). It is further related with a method of separating ssRNA species according to their size.

In a specific aspect, the invention is related to the separation of dsRNA from ssRNA, and/or separating ssRNA species according to their size, where the dsRNA and ssRNA are bound by noncovalent interactions to a primary amino solid phase.

In another specific aspect, the invention is related to separation of dsRNA from ssRNA by means of an ascending pH gradient in which dsRNA elutes at a lower pH value than ssRNA. Smaller ssRNA species elute at lower pH values than larger ssRNA species.

In a more specific aspect, the invention is related a pH gradient over a range of pH 3.5 to pH 11.5, or pH 4.5 to pH 11.5, pH 5.5 to pH 11.5, pH 6.5 to pH 11.5, or pH 7.5 to pH 11.5, or pH 8.5 to pH 11.5, or pH 8.5 to pH 11.0, or pH 8.5 to pH 10.5, or pH 8.5 to pH 10.0, or pH 8.5 to pH 9.5, or pH 8.5 to pH 9.0, or a higher range, or a lower range, or an intermediate range. A range of pH is specified because the value required to separate dsRNA from a particular ssRNA or to fractionate ssRNA species of differing size will depend upon their respective size. In one embodiment, the pH value may be increased continuously over a particular range forming a so-called linear gradient. In a related embodiment, the pH may be increased discontinuously in discrete steps, forming a so-called step gradient. In another related embodiment, the gradient may consist of a single step.

In another embodiment, elution by increasing pH may be conducted in the presence of salts for the purpose of increasing the recovery of ssRNA. In one such embodiment, the salt species may be sodium chloride at a concentration in the range of 10 mM to 250 mM, or 20 mM to 200 mM, or 50 mM to 100 mM. In another such embodiment, the salt species may be potassium chloride at a concentration within a similar range, or guanidine-HCl at a concentration within a similar range, or guanidine thiocyanate at a concentration within a similar range. The inclusion of salts during elution also causes ssRNA to elute at a lower pH value.

In another aspect, the invention is related with a method in which ssRNA bound to a primary amino solid phase is washed with a chelating agent.

In one embodiment, the chelating agent may be ethylenediaminetetraacetic acid (EDTA) at a concentration of 2 mM to 200 mM, or 5 mM to 100 mM, or 10 mM to 50 mM, or 20 mM to 25 mM, or a lower range, or intermediate range, or higher range up to full saturation. In closely related embodiments, the chelating agent may be a salt of citric acid, or phosphoric acid, or ethylene glycol-bis(2-aminoethylether)-N,N,N',N'-tetraacetic acid (EGTA), or tris(2-aminoethyl)amine, or another chelating agent, or a mixture of chelating agents over the same range of concentrations described for EDTA.

In one embodiment of the invention, treatment with chelating agents may include any of the following: the addition of chelating agents to the sample, buffer exchanging the sample into a metal ion-free buffer, buffer exchanging the sample into a chelated buffer, and employing metal ion-free or chelated buffers to conduct the steps of the method, including during pH elution.

In one aspect, the invention is related with the separation of dsRNA and ssRNA in which the primary amino solid phase is washed with salts to remove a subset of the dsRNA in advance of performing the final separation of dsRNA and ssRNA by means of increasing pH. In all such embodiments the concentration of salt during the wash is greater than the concentration of salt present during elution.

In one embodiment, a salt employed to wash the solid phase in advance of elution by increasing pH may be of any species of salt at any concentration, including up to full saturation. In one such embodiment where the salt is sodium chloride, which saturates at about 5.0 M, the concentration of salt may be in the range of 10 mM to 5 M, or 50 mM to 5 M, or 100 mM to 5 M, or 500 mM to 5 M, or 1 M to 5 M, or 2 M to 5 M, or 3 M to 5 M, or 4 M to 5 M, or an intermediate range but preferably in the range of 1 M to 5 M. In a closely related embodiment, the salt may be potassium chloride. It will be recognized that since RNA may be precipitated by high concentrations of neutral salts such as sodium chloride or potassium chloride, as well as by others such as lithium chloride. It will be further recognized that precipitation of RNA during sample application or during elution will be highly undesirable since it will likely interfere with flow of buffers through the solid phase chromatography device. Strictly speaking, this should not be a problem if the salt wash is conducted after sample loading and the excess salts are removed in advance of elution, however it will often be preferable to avoid the issue entirely by employing non-RNA-precipitating salts instead.

In one embodiment where RNA-precipitating salts are replaced with non-RNA-precipitating salts, the salt is a chaotropic salt such as guanidinium hydrochloride, which saturates at about 6 M, the concentration may be a value in the range of 10 mM to 6 M, or 50 mM to 6 M, or 100 mM to 6 M, or 500 mM to 6 M, or 1 M to 6 M, or 2 M to 6 M, or 3 M to 6 M, or 4 M to 6 M, or 5 M to 6 M, or an intermediate range but preferably in the range of 3 M to 4 M. In a closely related embodiment where the salt is a chaotropic salt such as guanidine thiocyanate, which saturates at about 12 M, the concentration may be a value in the range of 10 mM to 12 M, or 50 mM to 12 M, or 100 mM to 12 M, or 500 mM to 12 M, or 1 M to 12 M, or 2 M to 12 M, or 3 M to 12 M, or 4 M to 12 M, or 5 M to 12 M, or 6 M to 12 M, or 7 M to 12 M, or 8 M to 12 M, or 9 M to 12 M, or 10 M to 12 M, or 11 M to 12 M, or an intermediate range but preferably in the range of 1.5 M to 3.0 M. It will be apparent from the example of these two salts that other salts may be similarly employed in ranges up to but not exceeding the point of saturation.

In one embodiment, chelating agents may be used in conjunction with salts. In various embodiment of the invention, treatment with salts and/or chelating agents may include any of the following: the addition of salts and chelating agents to the sample, buffer exchanging the sample into a salt- and/or chelating agent-containing buffer, buffer exchanging the sample into a salt- and/or chelating agent-containing buffer, and employing a salt- and/or chelating agent-containing buffers to conduct the steps of the method, including elution of the ssRNA. In some such embodiments, the species of salts, chelating agents, and their respective concentrations may differ at each step of the method.

In some embodiments, dsRNA may be separated from ssRNA by equilibrating the sample to a high concentration of non-RNA-precipitating salt such as guanidine thiocyanate plus a chelating agent such as EDTA. The solid phase may be equilibrated to a buffer containing the same concentrations of guanidine thiocyanate and EDTA. During application of the sample to the solid phase, the majority of the dsRNA fails to bind to the solid phase. At the conclusion of a washing step with the same concentrations of guanidine thiocyanate and EDTA, dsRNA is reduced to trace levels. Guanidine thiocyanate and EDTA are then washed out of the system with a buffer that does not contain them. Any remaining dsRNA is separated from ssRNA in an increasing pH gradient.

In preparative embodiments where the objective is to isolate a quantity of purified ssRNA for some purpose, it will most often be desirable to neutralize the pH of the ssRNA soon after pH elution to minimize its exposure to pH values approaching pH 9 or above. Experimental data show that ssRNA exposed to alkaline conditions for only the period required to conduct the method of the invention retain their native composition and remain stable indefinitely. Essentially instantaneous neutralization can be performed by collecting the fractions into a neutralizing solution. Rapid neutralization may alternatively be performed by adding a neutralization solution immediately after fraction collection. Neutralization may also be performed after fraction collection by buffer exchange methods including chromatography or diafiltration. All of these methods are commonly practiced and well known in the art, for example in the field of affinity chromatography where post-elution pH neutralization of samples is routine.

The method of the invention may be practiced using any device which is customary in the art, e.g. the primary amino solid phase can be arranged in a chromatography device. Typically, the solid phase surface can be in the form of a monolith, a column of packed particles, a column of packed nanofibers, a membrane adsorber, or a hydrogel, among other chromatography formats.

The method may be employed for purpose of performing analytical or preparative applications. It is applicable to all mRNAs but especially valuable for mRNA in the size range of 1,000 bases to 25,000 bases. The specific chromatography conditions may vary according to the size of the RNA and the contaminant distribution in the applied sample. Adjusting the specific conditions to achieve the best analytical or preparative results for any particular ssRNA species employs the same experimental skills known to practitioners of the art of chromatography for decades.

The method of the invention may be preceded, or followed, or both by one or more additional processing methods to purify the ssRNA to a greater degree than can be achieved by any single processing method alone.

DETAILED DESCRIPTION OF THE INVENTION

Figure 1:
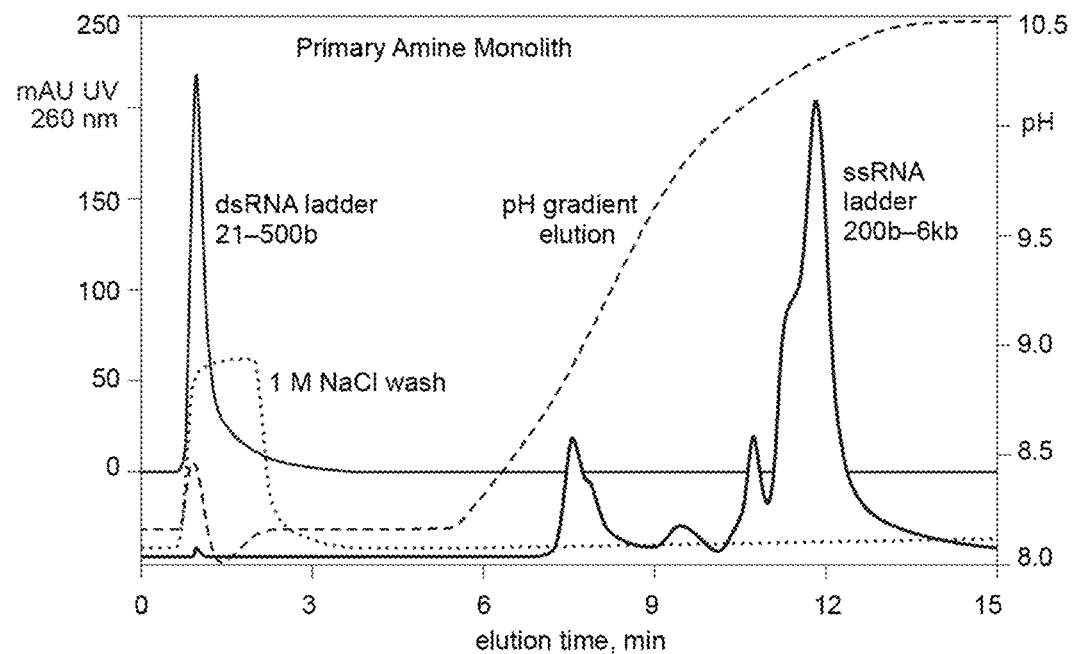
FIG. 1 depicts separation of dsRNA from ssRNA with a primary amino solid phase, with dsRNA eliminated by a sodium chloride step in advance of eluting ssRNA by means of a pH gradient at ambient temperature.

The term primary amino solid phase refers to a solid phase suitable for performing chromatography that dominantly or exclusively bears primary amino ligands on its surface(s). The terms "primary amino solid phase" or "solid phase bearing primary amino groups" or "primary amine-bearing solid phase" or "primary amino-bearing solid phase" or "primary amine solid phase" are synonymous and interchangeable. Secondary amines should be absent from the surface of the solid phase or present in a minority. Tertiary and quaternary amines should be absent or represent a small minority. Negatively charged residues should be absent. Uncharged hydrophobic or hydrogen bonding residues may be present.

The term "primary amino group" describes a nitrogen atom linked by a single covalent bond to each of two hydrogen atoms, and also linked by a single covalent bond to a carbon atom. The primary amino group may be covalently linked directly to a solid phase through the its carbon atom. Alternatively, the primary amino group may be linked indirectly to the solid phase by covalent attachment of its carbon atom to a so-called spacer arm that is covalently linked to the solid phase. A primary amino group may also be part of a polymeric structure covalently linked to the solid phase where the repeating subunits of the polymer include primary amino groups.

The solid phase may be a chromatographic solid phase in the form of one or more porous membranes, one or more fibers, one or more porous or non-porous particles, or a monolithic solid phase, including monoliths synthesized from a single polymer mixture, or so-called hydrogels which represent monoliths synthesized first as a macro-skeleton with a secondary ligand-bearing polymer phase synthesized on top of it (a so-called hydrogel). Any of these solid phase materials may be provided in a housing to facilitate performance of chromatography. Chromatographic solids phases in housings are commonly referred to as chromatographic devices and often as columns.

Chromatographic solid phases bearing primary amino groups are known and available commercially. One example is marketed under the name Toyopearl NH2-750F, manufactured by Tosoh Biosciences, where "NH2" refers to the primary amine [www.separations.eu.tosohbioscience.com/solutions/process-media-products/by-mode/ion-exchange/anion-exchange/toyopearl-nh2-750f]. Marketing materials indicate that the primary amino groups are in the form of a polyamine, meaning that it is a polymer with repeating primary amine subunits affixed covalently to the solid phase. Such polymers are typically linked to the surface of the solid phase through one or more of their primary amino groups. This linkage has the effect of converting the linking amino residues from primary amino groups to secondary amino groups, thereby producing a mixture of primary amino groups and secondary amino groups on the surface of the solid phase.

Another example is manufactured by Sartorius under the name Sartobind STIC PA, where "PA" refers to the primary amine [www.sartorius.com/shop/ww/en/usd/sartobind-stic®-pa/c/M_Sartobind_STIC_PA]. Marketing materials indicate that the primary amino group is in the form of a polymer, specifically polyallylamine, with repeating primary amino subunits, affixed covalently to the solid phase. As with the previous product, such polymers are typically linked to the surface of the solid phase through one or more of its primary amino groups. This linkage has the effect of converting the linking amino residues from primary amino groups to secondary amino groups, thereby producing a mixture of primary amino groups and secondary amino groups on the surface of the solid phase.

All major commercial producers of chromatographic solid phases manufacture products with amine derivatives on their surfaces, including anion exchangers, indicating the requisite knowledge and resources in the field to produce positively charged solid phase dominantly bearing primary amino groups on a regular or experimental basis.

Given that chromatographic solid phases bearing primary amino groups may not be named in a manner that clearly or fully reveals their composition, it will be useful to have a simple analytical method to determine if a given chromatography solid phase has appropriate characteristics to practice the invention. One simple method for making this determination is to equilibrate the chromatographic solid phase in question with a buffer such as 50 mM Tris, pH 7.5, then inject a sample consisting of a so-called ssRNA ladder containing subsets of RNA molecules each with a different size. Such RNA ladders commonly cover sizes ranging from 50 to 500 bases, or 100 to 1000 bases, or 200 to 6000 bases, or some other range, and are available commercially from common suppliers such as Thermo Scientific and New England BioLabs. After sample injection and a brief wash with equilibration buffer to displace unbound sample components, elute the primary amino chromatography device with a linear pH gradient from pH 7.5 to about pH 11. Primary amino solid phases will elute ssRNA species in order of increasing size as illustrated in FIG. 1. If ssRNA does not elute or only the smallest species elute, that is a probable indication that the solid phase contains an excessive proportion of non-primary amino groups, including any one of or any combination of secondary amino groups, tertiary amino groups, and quaternary amino groups.

The term "RNA size" or "size of RNA" refers to the number of bases in the nucleotide strand. Bases are commonly noted as "b". Thus the designation 100 b refers to an RNA strand of nucleotide 100 bases. RNA size is independent of RNA conformation, referring to single-stranded (ssRNA) and double-stranded (dsRNA). A given in vitro transcription mixture, referring to the mixture of reagents and product and byproducts produced during synthesis of mRNA, may contain both ssRNA and dsRNA, but both will be of the same size with respect to the number of bases because both are derived from the same DNA plasmid. In some cases, ssRNA strands may become clipped or truncated during processing, either though shear stress or enzymatic lysis, resulting in formation of fragmentary subpopulations of the previously complete strand. In other cases, truncated forms could hypothetically arise from incomplete transcription. Whatever the source, the ability of the method of the invention to fractionate ssRNA according to size provides a tool for removal of undesired fragmentary forms.

The term "equilibrated" or "equilibration" refers to a chemical conditioning step having been performed on the solid phase and/or on the sample to create a specific chemical environment. Solid phases are customarily conditioned by exposing them to a buffer that embodies the desired pH and salt composition. Samples are customarily conditioned by titration of pH, sometimes by dilution to reduce the salt concentration, and sometimes by buffer exchange techniques including by chromatography, or by dialysis, or by diafiltration with tangential flow filtration membranes. All of these methods and the criterial for choosing one or another have been known in the art for decades.

The term "loading" or "sample application" refers to the process of bringing the equilibrated sample into contact with the equilibrated positively charged solid phase dominantly bearing primary amino groups. This is usually done with chromatography devices by causing the sample to pass through the device by means of an external force, such as by gravity or by pumping.

The term "adsorption" refers to the process of binding a biological product to a chemically complementary surface. Adsorption is distinct from absorption which can be likened to uptake of water by a sponge through the physical action of capillarity but not involving a chemical interaction. Complementarity in the present case is understood to involve electrostatic charge. The negative electrostatic charge on the surface of RNA mediates its adsorption to the surface of a solid phase that has been rendered electropositive by virtue of the primary amino groups on its surface. Adsorption of biological products to chromatographic solid phases is often referred to by the more familiar term "binding".

The term "selective adsorption" refers to conditions that permit adsorption of at least one species while preventing adsorption of one or more other species. In the present case, operating conditions may be adjusted to prevent the binding of dsRNA while permitting ssRNA to bind. The term "desorption" refers to the process of releasing a biological product from a chemically complementary surface to which it has been previously adsorbed. For the method of the invention, desorption of ssRNA will usually require an alkaline pH value of at least pH 9.0, or pH 9.5, of pH 10.0, or higher. Salts may be used to enhance desorption, typically with the effect of achieving elution of a given ssRNA species at a lower pH than in the absence of salt. However, no salt or combination of salts at any concentration will achieve elution of large ssRNA at acidic or neutral pH.

The term "selective desorption" refers to situations in which one or more adsorbed species are released from the solid phase surface by a change in the conditions that leaves one or more other species still adsorbed. A yet-different set of conditions can then be applied to release a different subset of species from the solid phase surface. In one such instance, the majority of dsRNA might be removed from the primary amino solid phase by application of a high concentration of salt at neutral or near neutral pH while ssRNA remains bound. The dsRNA would be said to have been selectively desorbed. The ssRNA would be selectively desorbed in a follow-on step at alkaline pH, possibly in the presence of salt.

The term "washed" refers to a process of exposing the loaded column to clean buffer for the purpose of displacing unbound species from pores or channels within the device. The term "rinsed," in the present context, has the same meaning. In the most basic case, the wash buffer has the same formulation as the equilibration buffer. In more complex configurations, a wash buffer may have the additional role of chemically releasing a subset of weakly bound contaminants from the solid phase so that they can be removed before the desired product is eluted. Or there may be more than one washing step where the first employs conditions identical to the equilibration buffer but the second employs conditions that displace a subset of weakly bound contaminants from the solid phase so that they can be removed before elution. Washing can also be used to transition to a buffer that will enable elution under a different or more controlled set of conditions. For example, after a contaminant-displacing high-salt wash, it may be desirable to perform a no-salt wash to set up the conditions to elute ssRNA in a no-salt ascending pH gradient. Lacking that wash, elution would begin by default at high salt, creating a gradient in which salt concentration descends while pH ascends.

The term "elution" represents a special case of the term "desorption" pertinent to the field of chromatography. It refers to a process of changing the chemical environment in which the solid phase resides to cause dissociation of the interaction between the primary amino solid phase and the species that remain bound after the load and wash steps. With dsRNA removed from the solid phase, ssRNA may be eluted by a simple increase of pH, or by an increase of pH in conjunction with salts.

Elution may be conducted in one or a series of steps in which each step decreases the strength of the interaction between the solid phase and the ssRNA. Changes in conditions may also be made in a continuous or linear manner, causing weakly bound species to be desorbed early in the continuum while strongly bound species elute later in the continuum. Whether in a step or linear format, changes in operating conditions are commonly referred to as gradients and particularly as elution gradients. Step gradients are often considered more convenient but linear gradients typically support better reproducibility.

The term "ambient temperature" is generally considered analogous to the expression "room temperature" or "ordinary temperature". It typically corresponds to a temperature in the range of about 20-22° C. but may also include a broader range such as about 18-25° C.

The term "chaotropic salt" refers to a salt species for which at least one of its constituent ions has a high chaotropic ranking in the Hofmeister series of lyotropic and chaotropic ions. Lyotropic ions reside at one end of the Hofmeister series. Chaotropic ions populate the opposite end of the series. Chaotropic ions are often described as being preferentially bound by biomolecules. Chaotropic salts have the effect of relaxing non-covalent interactions within and among biomolecules, sometimes to the extent of destabilizing overall structure and dissociating interactions among the respective elements in multicomponent noncovalent mixtures. They usually have the effect of increasing solubility. Examples of chaotropic salts include guanidinium salts, thiocyanates, and perchlorates, among others. In some cases, both the anion and cation of a particular salt are strongly chaotropic as in the case of guanidine thiocyanate. Such salts have more chaotropic potential than salts including only a chaotropic anion or chaotropic cation. Lyotropic ions reside at the opposite end of the Hofmeister series. They are often described as being preferentially excluded by biomolecules. Lyotropic ions have the effect of stabilizing biomolecules, favoring non-specific association among individual elements of mixtures. Strongly lyotropic ions usually decrease solubility of large biomolecules. Examples of lyotropic salts include ammonium sulfate, potassium phosphate, and sodium citrate, among others. Salts that represent intermediates in the Hofmeister series tend to have moderate or little influence on stability, association-dissociation, or solubility on biomolecules. Examples include so-called neutral salts such as sodium chloride and potassium chloride. To the extent that neutral salts may affect stability, association-dissociation, or solubility, their influence is mediated predominantly through coulombic (electrostatic) forces.

The term "multivalent metal cation" refers the positively charged ionic form of a metal where the net charge of the ion is two or greater. Multivalent metal cations include calcium, magnesium, and zinc, all of which have a net charge of 2+, and ferric iron with a net charge of 3+, among others with similar or different valencies. All of these ions have an affinity for nucleic acids which they bind through coordination bonds. Coordination bonds are 15-60 times stronger than ionic bonds, which means that binding of multivalent metal cations to nucleic acids or other biomolecules persists even at saturating concentrations of salts. Multivalent metal cations can be problematical in the purification of RNA because they can promote formation of dsRNA sequences or stabilize existing dsRNA sequences. They can also promote formation of complexes or stabilize existing complexes (associations), among multiple RNA molecules, between RNA and DNA molecules, and among RNA, DNA, and protein contaminants.

The term "chelating agent," in the context of the method of the invention, refers to a molecule with the ability to form such strong coordination bonds with multivalent metal cations that they are able to competitively remove those metal ions from previous associations with biomolecules, including nucleic acids, including mRNA.

The term "nuclease" or "nuclease enzyme" refers to proteins that have the ability to cleave the chains of nucleic acids, ideally into individual nucleotides, doublets, or triplets. There are two major classes: DNAse enzymes that lyse DNA, and RNAase enzymes that lyse RNA. RNAses are to be strictly avoided because they will destroy the ssRNA product. DNAses are often used to simplify purification by destroying the DNA plasmid template used to produce mRNA. DNAse enzymes frequently require the use of a multivalent metal cation co-factor to function properly. Multivalent metal cations can interfere with RNA purification as discussed above.

The term "protease" or "proteinase" or "proteolytic enzyme" refers to a protein that has the ability cut other proteins into small fragments. This is sometimes used as a method of reducing protein contamination ahead of chromatography steps that might be burdened by such contamination. Many proteases, such as trypsin require a multivalent metal cation co-factor to function properly. Multivalent metal cations can interfere with RNA purification as noted above. Proteases commonly employed for this purpose include proteinase K which provides good results even in the absence of a multivalent metal cation co-factor.

The decision to include salts during the performance of the method may reside partly in the choice of a follow-on analytical method or purification step, if one is desired or required. For example, if the follow-on method is intolerant of salt, it will be advantageous to elute the ssRNA from the positively charged solid phase dominantly bearing primary amino groups in the absence of the salt or at a sufficiently low salt concentration to avoid interference. If the follow-on method is highly tolerant of salt, then elution of the device may employ a substantial concentration of the salt species tolerated by the follow-on step.

In one embodiment, the inclusion of 50 mM NaCl in the pH gradient endpoint buffer causes the ssRNA to elute at a lower pH than when NaCl is absent from the endpoint buffer. The presence of 50 mM NaCl in only the gradient endpoint buffer suggests that rather than eluting in an exclusively pH gradient, the ssRNA is eluted by a simultaneous gradient of increasing NaCl and increasing pH. In a closely related embodiment, the inclusion of 100 mM NaCl in the pH gradient endpoint buffer causes the RNA to elute at a lower pH than when the gradient endpoint buffer includes 50 mM NaCl. In both cases, the recovery of ssRNA increases significantly when NaCl is included in the gradient endpoint buffer. Separation between dsDNA and ssRNA is widest at 0 mM NaCl. It diminishes when the endpoint buffer contains 50 mM NaCl, and diminishes further when the endpoint buffer contains 100 mM NaCl, but the separation remains good at 100 mM. Similar concentrations of other salts may be substituted, including chaotropic salts, and chelating salts.

In one embodiment, pH gradient elution from the primary amino solid phase is performed to separate ssRNA species according to their size, with smaller species eluting earlier in the gradient than larger species.

The following series of general non-limiting descriptions of basic method options illustrates variations in how the method may be performed and provides a platform for more detailed discussion of operational variables. It is understood that the buffer conditions mentioned in each of these scenarios are intended to provide a general idea of how the method may be practiced and that optimization of buffer formulations will be required to accommodate ssRNA species of different sizes and with different contaminant loads.

In one embodiment, a primary amino solid phase in the form of a chromatography device such as a monolith is equilibrated to a pH value close to neutrality, such as 20 mM Tris, 20 mM bis-tris-propane, pH 7.5±0.5. A sample containing a mixture of dsRNA and ssRNA is equilibrated by buffer exchange to 20 mM Tris, 20 mM bis-tris-propane, 20 mM glycine, pH 7.5±0.5. The chromatography device is then eluted with a linear pH gradient from the equilibration buffer to an endpoint buffer of 20 mM Tris, 20 mM bis-tris-propane, 20 mM glycine, 100 mM NaCl, pH 11±0.5 over 20 device-volumes, or over 50 device-volumes, or over 100 device volumes, where the number of device volumes is used as a means of adjusting the rate at which pH changes during the gradient, in other words the slope of the gradient. This approach may be particularly useful for analytical applications because dsRNA, ssRNA, DNA fragments, and proteins will all bind to the primary amine-bearing solid phase and elute within the gradient, thus providing an indication of the total contents of the sample; product and contaminants. This approach may also be used as starting point for development of conditions for preparative separations.

In a different embodiment, a primary amine solid phase may be loaded under the same conditions then washed with a solution of 3 M NaCl to remove the majority of dsRNA, DNA, and protein contamination. The NaCl is then itself be removed by a follow-on wash lacking excess salt so that pH gradient elution of ssRNA begins in the absence of excess salt. Comparison of results with the previously-described embodiment will permit evaluation of the extent to which the NaCl wash improves the purity of the ssRNA. Determination of the most favorable concentration of NaCl is a routine exercise well known in the art of chromatography, where the objective is to achieve the best balance of product purity and product recovery.

In closely related embodiments, either or both of the previous embodiments may include 50 mM sodium chloride in the pH gradient buffers. In other closely related embodiments, 100 mM sodium chloride may be included in the pH gradient buffers. In other closely related embodiments, any other salt may be substituted for sodium chloride.

In another related embodiment, a primary amino solid phase may be loaded with the same conditions then washed with a solution of 3 M guanidine-HCl to remove the majority of dsRNA in advance of eluting the desired ssRNA product by means of a pH gradient. The guanidine wash is followed with a wash lacking guanidine salt so that pH gradient elution of ssRNA begins in the absence of excess salt. In a closely related embodiment, 100 mM sodium chloride may be included in the pH gradient buffers. In another closely related embodiment, guanidine-HCl may be replaced by guanidine isothiocyanate. Comparison of results with the two previously-described embodiments will permit evaluation of the extent to which the guanidine wash improves the purity of the ssRNA.

In a related embodiment representing an extension of the above series, a chelating agent such as but not limited ethylenediaminetetraacetic acid (EDTA) at a concentration of 20 mM may be combined with guanidine, with the intention of dissociating metal-stabilized complexes and displacing the non-ssRNA species from the solid phase in advance of eluting the ssRNA. Comparison of results with the three previously-described embodiments will permit evaluation of the extent to which, if any, the chaotrope-chelator wash improves the purity of the ssRNA.

In other related embodiments, washes with other salt species or combinations of salt species at various pH values may be evaluated to maximize clearance of dsRNA in advance of eluting the ssRNA. The underlying concept will generally to apply the highest concentration of the most dissociative salt at the highest pH that does not cause elution of ssRNA, with the notion that such conditions are likely to remove the largest subset of undesired contaminants in advance of eluting the desired ssRNA. Later adjustments can be made to determine the minimum salt concentration required to achieve desired effect.

In some embodiments, the slope of a linear pH gradient may be modified to alter the degree of separation among species eluting in that gradient, or particularly to improve fractionation among ssRNA molecules of different sizes. If eluting with a pH gradient of 10 device volumes does not produce the desired degree of separation, its duration may be extended to 20 device volumes, or 50, or 100 device volumes or more.

In some embodiments, the increase of pH to elute the desired ssRNA and separate it from dsRNA may be conducted in steps. If dsRNA content has been sufficiently reduced in the previous wash steps, then the ssRNA can be eluted in a single step for the purpose of simplifying the method and obtaining the eluted ssRNA at the highest possible concentration and in the lowest possible volume. Step elution may alternatively be conducted in a succession of step of increasing pH. The individual steps may be relatively modest or they may be large according to the needs of a particular preparation. In some embodiments, the increase of pH to elute the desired ssRNA may be conducted in a single step.

In one embodiment, a sample containing dsRNA and ssRNA may be loaded onto a primary amino solid phase at a pH that precludes binding by the majority of the dsRNA. In some such embodiments, depending on the size of the mRNA, the pH during sample loading may be pH 8.0, or pH 8.5, or pH 9.0, or a higher pH that does not prevent binding of ssRNA.

In an embodiment representing a special case, ssRNA may be eluted by a salt gradient at constant pH. This will require first that the pH be elevated to a point just beneath the value at which the ssRNA would elute in the absence of salt. Then the salt gradient will be applied at that pH. This embodiment bears superficial similarity to the standard anion exchange elution format of salt gradients at fixed pH but it remains distinctive in the field of separating dsRNA from ssRNA because salt gradients for large mRNA are otherwise successful only at elevated operating temperatures.

Many methods of equilibrating samples to the conditions for loading them onto chromatography columns are known to persons of skill in the art. Any of these methods may be employed without altering the true nature of the method. Among these methods are the laboratoryscale method of dialysis, the method of diafiltration with tangential flow filtration membranes, and the method of buffer exchange chromatography. In some cases, adequate sample equilibration may be achieved by titrating the sample to the target pH and, if necessary, diluting the sample with water or with a low-salt or non-salt containing buffer.

In one embodiment, separation of dsRNA from dsRNA by means of increasing pH may be augmented by the presence of a sugar to compete with hydrogen bonding between the ssRNA and the primary amino groups of the solid phase with the expected result of causing ssRNA to elute at a lower pH than in the absence of a sugar. In one such embodiment the sugar is sorbitol, or xylitol, or mannitol, trehalose, or sucrose, or another sugar or combination of sugars. In some such embodiments, the concentration of the sugar may range from 0.1% to 20%, or 1% to 20%, or 5% to 20%, or 10% to 20%, or a value within a higher, lower, or intermediate range.

In a related embodiment, separation of dsRNA from dsRNA by means of increasing pH is augmented by the presence of a nonionic chaotrope to compete with hydrogen bonding between the ssRNA and the primary amino groups of the solid phase with the expected result of causing the ssRNA to elute at a lower pH than in the absence of a chaotrope. In one such embodiment the chaotrope is urea. In some such embodiments, the concentration of urea may range from 0.1 M to 10 M, or 1 M to 9 M, or 2 M to 8 M, or 4 M to 6 M, or a value within a higher, lower, or intermediate range. In another such embodiment the chaotrope is dimethyl sulfoxide. In some such embodiments, the concentration of dimethyl sulfoxide is up to 99%. In other related embodiments, a nonionic chaotrope may be applied during a wash step in advance of eluting the desired ssRNA by means of a pH gradient.

In another embodiment, separation of dsRNA from dsRNA by means of increasing pH is augmented by the presence of an alkaline amino acid with the expected result of causing ssRNA to elute at a lower pH than in the absence of an alkaline amino acid. In one such embodiment, the alkaline amino acid is histidine, or histamine, or lysine, or arginine, or another alkaline amino acid or a mixture of alkaline amino acids. In one such embodiment, the concentration of histidine may be in the range of 1 mM to 250 mM, or 10 mM to 250 mM, or 20 mM to 250 mM, or 50 mM to 250 mM, or 100 mM to 250 mM, or a value within a higher, lower, or intermediate range. In another such embodiment, the concentration of lysine may be 1 mM to 10 M, or 10 mM to 10 M, or 100 mM to 10 M, or 1 M to 10 M, or a value within a higher, lower, or intermediate range. In another such embodiment, the concentration of arginine may be in the range of 1 mM to 850 mM, or 10 mM to 850 mM, or 100 mM to 850 mM, or 425 mM to 850 mM, or a value within a higher, lower, or intermediate range.

Nucleic acids, including mRNA, are known to have a high affinity for multivalent metal cations. They form strong associations with each other principally through coordination bonding between the metal ions and the negatively charged phosphatidic acid residues along the backbone of nucleic acids. Calcium and magnesium are both known to participate in such interactions and both are divalent metal cations, having a charge of 2+. Ferric iron, a trivalent cation with a charge of 3+, interacts even more aggressively with nucleic acids. At each point where any one of these ions interacts with a nucleic acid, it neutralizes an equivalent number of negative charges. This creates a superficial expectation that the negative charge on a given mRNA molecule would be reduced and weaken the interaction of the mRNA with an anion exchanger. Instead, addition of multivalent metal cations typically results in the formation of non-specific cross-links that cause ssRNA to form large aggregates that do not elute from a primary amine-bearing solid phase in a pH gradient.

Since multivalent metal cations are commonly added to mRNA preparation, it is recommended that steps be taken in all embodiments to reduce the content and preferably eliminate multivalent metal cations entirely from samples before loading them onto a positively charged solid phase dominantly bearing primary amino groups; or at least take steps to remove them before the device is eluted. There are at least two additional reasons for removing them in advance. The first reason is that they may tend to promote formation or stabilization of intrachain and interchain dsRNA sequences. The second reason is that metal ions stabilize non-specific associations between nucleic acids and proteins, essentially forming a stable bridge between them. Since coordination bonds range from 15 to 60 times stronger than ionic bonds, coordination complexes easily survive exposure to even saturating levels of non-metal salts, including NaCl and guanidinium salts. This makes extraction of multivalent metal cations, so far as possible, essential to obtain the highest ssRNA purity and recovery from the method of the invention. Given effective extraction of multivalent metal cations, effective dissociation of nucleic acid-protein complexes can be achieved with high concentrations of chaotropic salts such a guanidinium salts, and to a lesser degree with high concentrations of non-chaotropic salts such as NaCl. Lyotropic salts are likely to impose a contrary influence.

In some embodiments where chelator or chelator-high-salt dissociation of nucleic acid-metal-contaminant complexes is performed during sample preparation and/or a chelator or chelator-chaotrope wash is performed, it may be followed by a washing step that is free of salts beyond the agents used to provide pH control. This will enable the ssRNA to be eluted in a low salt environment.

In other embodiments, chelating agents and high salt concentrations may be maintained during elution of the ssRNA by increasing pH. In other embodiments, the chelating agent may be eliminated while the high salt is maintained. In other embodiments the high salt may be eliminated while the chelating agent is maintained.

A particular benefit of the invention is that its ability to remove DNA plasmids from ssRNA preparations makes it unnecessary to perform nuclease digestion of an in vitro transcription mixture, or partially purified in vitro transcription mixture. This has disproportionately high value because the nuclease digestion requires addition of magnesium ions in order for the enzyme to be active. Those magnesium ions potentially contribute to cross-linking of the desired ssRNA, with itself and with other sample components, with the practical result that the recovery of the desired ssRNA product is reduced. By making nuclease digestion unnecessary, addition of magnesium ions becomes unnecessary, and recovery of ssRNA is uncompromised.

To the extent that nuclease digestion might be desired despite the ability of the method of the invention to separate plasmid DNA from ssRNA, it may be performed, then the positively charged solid phase dominantly bearing primary amino groups can be washed with an excess of chelating agent to displace residual magnesium ions. In one such embodiment, following nuclease digestion of plasmid DNA in the presence of 5 mM nuclease enzyme, a chelating wash containing EDTA in the range of 10-50 mM EDTA, or more, may be performed.

In one embodiment beginning with an in vitro transcription mixture, EDTA is added to a final concentration of 10-50 mm for the purpose of scavenging multivalent metal cations. Assuming the pH is in a range between pH 7 and pH 8.0, the sample can be filtered if necessary, then loaded to a primary amino chromatography device equilibrated to 50 mM Tris, 100 mM NaCl, 10 mM EDTA, pH 8.0. After sample loading, the device is washed with 50 mM Tris, 3 M guanidine-HCl, 20 mM EDTA, pH 8.0 for 10-20 device volumes. The column is then washed with 20 mM Tris, 20 mM bis-tris-propane, 20 mM glycine, pH 8.0 to flush guanidine and EDTA out of the device and prepare for elution of the ssRNA. The ssRNA is then eluted with a 50 device volume linear gradient to 20 mM Tris, 20 mM bis-tris-propane, 20 mM glycine, 250 mM arginine, pH 11.0. Immediately after fraction collection, the vessels containing the ssRNA peak are neutralized by addition 1 M acetic acid.

In one embodiment representing an extension of the above embodiment, the neutralized sample after the method of the invention is applied to an Oligo dT affinity chromatography device for final purification.

In an alternative embodiment representing an extension of the above embodiment, the neutralized sample is applied to a hydrophobic interaction chromatography device for final purification.

In one embodiment beginning with an in vitro transcription mixture, the mixture is precipitated by addition of lithium chloride (LiCl) to a final concentration of 2.0 M to 2.5 M. The supernatant is discarded and the precipitate is resuspended with 50 mM Tris, 100 mM NaCl, 20 mM EDTA, pH 8.0 and filtered if necessary to remove turbidity. The sample is then loaded to a primary amino solid phase equilibrated to 50 mM Tris, 100 mM NaCl, 10 mM EDTA, pH 8.0. After sample loading, the device is washed with 50 mM Tris, 1.5 M guanidine isothiocyanate, 20 mM EDTA, pH 8.0 for 10-20 device volumes. The column is then washed with 20 mM Tris, 20 mM bis-tris-propane, 20 mM glycine, 100 mM NaCl, pH 8.0 to flush guanidine and EDTA out of the device and prepare for elution of the ssRNA. The ssRNA is then eluted with a 50 device volume linear gradient to 20 mM Tris, 20 mM bis-tris-propane, 20 mM glycine, 100 mM NaCl, pH 11.0. Immediately after fraction collection, the vessels containing the ssRNA peak are neutralized by addition 1 M acetic acid to a final proportion of 5% of the fraction volume. In a closely related embodiment, mRNA is precipitated with NaCl or another salt in place of LiCl. In another closely related embodiment, the mRNA is precipitated by adding ethanol to a final proportion of about 2.5%.

Industrial process developers often prefer to avoid the use of enzymes because the increase the expense of a process and because anything that is put in must later be removed and testing must be performed to document that it was removed. However, the use of enzymes early in a development program may be an expedient shortcut that permits a company to enter clinical trials earlier, and later develop a more advanced version of the process that does not require the use of enzymes. As noted above, in vitro transcription mixtures are commonly treated with DNAase enzymes to eliminate the DNA plasmid used as a template for production of mRNA. RNA purification may also use proteolytic enzymes to lessen the protein contaminant load in a given in vitro transcription. In some embodiments, an in vitro transcription mixture may be treated first with DNAse to eliminate the plasmid, and then with a proteolytic enzyme such as proteinase K to eliminate the DNAse and the bulk of other protein contaminants in advance of deploying the method of the invention. In other embodiments, because the method of the invention makes it unnecessary to employ DNAse, an in vitro transcription mixture may be treated exclusively with proteinase K or another proteolytic enzyme.

In one embodiment, an in vitro transcription mixture is treated with proteinase K to reduce the protein load. The sample is filtered through a membrane filter to remove particulates and then loaded to a primary amino solid phase equilibrated to 50 mM Tris, 10 mM EDTA, pH 8.0. After sample loading, the device is washed with 50 mM Tris, 3 M guanidine-HCl, 20 mM EDTA, pH 8.0 for 10-20 device volumes. The column is then washed with 20 mM Tris, 20 mM bis-tris-propane, 20 mM glycine, 50 mM NaCl, pH 8.0 to flush guanidine and EDTA out of the device and prepare for elution of the ssRNA. The ssRNA is then eluted with a 50 device-volume linear gradient to 20 mM Tris, 20 mM bis-tris-propane, 20 mM glycine, 50 mM NaCl, pH 11.0. Immediately after fraction collection, the vessels containing the ssRNA peak are neutralized by addition 1 M acetic acid.

In one embodiment, an in vitro transcription mixture is treated with 2 M guanidine isothiocyanate and 20 mM EDTA. The pH is adjusted, if necessary, to 7.5±0.5, and the sample filtered, if necessary to remove solids. A primary amino solid phase is equilibrated with 2 M guanidine isothiocyanate and 20 mM EDTA in 20 mM Tris, 20 mM bis-tris-propane, and 20 mM glycine, pH 8.0. The sample is loaded onto the solid phase then chased with equilibration buffer until the UV absorbance approaches zero. The solid phase is then washed with 20 mM Tris, 20 mM bis-tris-propane, 20 mM glycine, 50 mM NaCl, pH 8.0, then eluted with a pH gradient to 20 mM Tris, 20 mM bis-tris-propane, 20 mM glycine, 20 mM EDTA, pH 11.0. The gradient may be performed as a single step, a series of steps, or in a continuous (linear) format. Immediately after fraction collection, the vessels containing the ssRNA peak are neutralized by addition 1 M acetic acid.

Although the invention offers the benefit of suspending the need to perform separation of dsRNA and ssRNA at elevated temperature, it does not preclude the possibility of doing so. In some embodiments, the sample may be equilibrated to an elevated temperatures such as 37° C., 45° C., 56° C., 60° C., 70° C., or an intermediate, higher, or lower temperature in advance of performing the method at ambient temperature.

In some embodiments, the method of the invention may be conducted at elevated temperatures such as 37° C., 45° C., 56° C., 60° C., 70° C., or an intermediate, higher, or lower temperature. In such embodiments, ssRNA will elute at a lower pH than it does at ambient temperature.

In some embodiments, the sample may be equilibrated to an elevated temperature and the method may be performed at an elevated temperature.

In one embodiment, the method of the invention may be combined with the method of affinity chromatography using an Oligo dT (OdT) ligand. The two methods may be combined in any sequence desired.

In one embodiment, the method of the invention may be combined with the method of hydrophobic interaction chromatography (HIC). The two methods may be combined in any sequence desired. In one such embodiment, the hydrophobic ligand on the HIC solid phase may consist of a phenyl group. In another such embodiment, the hydrophobic ligand on the HIC solid phase may consist of a butyl group. In another such embodiment, the hydrophobic ligand on the HIC solid phase may consist of a hexyl group. In other such embodiments, the hydrophobic ligand on the HIC solid phase may consist of a different aliphatic or aromatic group, or a group that embodies both aliphatic and aromatic properties.

In one embodiment, the method of the invention may be combined with the method of reverse phase chromatography (RPC). The two methods may be combined in any sequence desired. In one such embodiment, the hydrophobic nature of the solid phase surface may be conferred by the native hydrophobicity of the styrene divinylbenzene (SDVB) polymer used to synthesis the solid phase. In another such embodiment, the hydrophobic nature of the solid phase surface may be conferred by the hydrophobicity of a ligand affixed to the surface of the solid phase, where that ligand represents an aliphatic hydrocarbon, or an aromatic hydrocarbon, or a ligand of mixed aliphatic-aromatic character.

In one embodiment, the method of the invention may be combined with the method of hydroxyapatite chromatography. The two methods may be combined in any sequence desired.

In one embodiment, the method of the invention may be combined with affinity chromatography using an OdT ligand and with RPC. The three methods may be performed in any sequence desired.

In one embodiment, the method of the invention may be employed to remove ssRNA from preparations of DNA plasmids. In a closely related embodiment, the method of the invention may be employed to remove ssRNA from a protein preparation. In one such embodiment, the method may be employed to remove contaminating ssRNA from enzyme preparations employed for synthesis of mRNA. In any of these embodiments, the sample may be loaded at acidic-to-neutral pH conditions and low salt concentration under which DNA and proteins bind to the positively charged solid phase dominantly bearing primary amino groups. They can then be eluted with a salt gradient to increase their degree of purity with respect to contaminants while leaving ssRNA bound to the surface of the solid phase. In closely related embodiments where the intent is solely to remove ssRNA, the sample and solid phase conditions may include a high concentration of salt at acidic-to-neutral pH that causes DNA and proteins to flow through the solid phase while the RNA is bound.

In one embodiment, the method of the invention may be used as an analytical tool to quantitate the amount of ssRNA in a sample. In one such embodiment, a sample at acidic-to-neutral pH may be mixed with a high concentration of salt so that most non-ssRNA molecules fail to bind. The primary amino solid phase may then be eluted by an increasing gradient of pH to sort the bound ssRNA by increasing size. In a closely related embodiment, the primary amine solid phase may be eluted in a single step to a sufficiently alkaline pH to elute all ssRNA in a single peak for the purpose of maximizing the sensitivity of the assay. In a related embodiment, the primary amine solid phase may be eluted with a linear gradient to 25 mM NaOH, or 50 mM NaOH, or 100 mM NaOH, or a higher, lower, or intermediate concentration. concentration. In another such embodiment, the primary amino solid phase may be eluted in incremental steps to 25 mM NaOH, or 50 mM NaOH, or 100 mM NaOH, or a higher, lower, or intermediate concentration. In another such embodiment, the primary amino solid phase may be eluted with a single step to 25 mM NaOH, or 50 mM NaOH, or 100 mM NaOH, or a higher, lower, or intermediate concentration. In any of the above embodiments, after loading the sample onto the primary amino solid phase, a dye that interacts with RNA to produce fluorescence may be injected, and the fluorescent dye-RNA complex passed through a fluorescence monitor to amplify the sensitivity of the assay. In one such embodiment, the dye may be Ribogreen.

In one embodiment, the method of the invention may be provided in the form of a kit to facilitate its practice. The kit will include two or more solid phases, at least one of which is a primary amine solid phase, and instructions describing the method of the invention. In one such embodiment, a second solid phase would be an Oligo-dT chromatography device. In another such embodiment, a second solid phase would be a hydrophobic interaction chromatography device. In another such embodiment, a second solid phase would be an Oligo-dT chromatography device and a third solid phase would be a hydrophobic interaction chromatography device.

In a typical protocol of a purification of mRNA with a solid phase as used according to the invention, a Primary Amine Monolith is used as follows.

The Primary Amine Monolith purifies large single-stranded mRNA (ssRNA) under aqueous conditions at ambient temperature. It removes dsRNA, DNA, proteins, and endotoxins while fractionating ssRNA in order of increasing size (FIG. 1). It can be used for one-step purification of research grade ssRNA or as a high-resolution capture step in a multi-step purification process. It also enables fast high-resolution analytical characterization of in vitro transcription mixtures, partially purified samples, chromatography fractions, and formulated drug substance.

The Primary Amine Monolith employs a unique combination of anion exchange and hydrogen bonding that purifies ssRNA in an ascending pH gradient. DNA, proteins, and dsRNA elute in advance of ssRNA. Purification performance is enhanced by a high-salt wash that removes the majority of dsRNA, DNA, and proteins in advance of elution. Remarkably, ssRNA remains bound even at saturating concentrations of chaotropic salts. Inclusion of a chelating agent during the high-salt wash further enhances contaminant elimination and leaves the pH gradient to remove the trace-level contaminants and aggregates that remain.

The ssRNA fraction from the Primary Amine Monolith can be further purified if desired by affinity chromatography using CIMmultus Oligo dT, by hydrophobic interaction chromatography using CIMmultus C4 HLD, or by reverse phase chromatography using CIMmultus SDVB (Contact BIA Separations for more information on any of these columns). The Primary Amine Monolith may also be used as a polishing method, especially after a high-salt step like precipitation or hydrophobic interaction chromatography, since high-salt samples can be loaded without further sample preparation.

The Primary Amine Monolith is a radial flow chromatography device. It is designed to distribute flow from the outside of the cylinder to the inside. This has the effect of stabilizing the physical structure of the cylinder and also has a concentration effect during elution that improves separation performance. Before conducting any experiments, be sure to connect the unit to the chromatograph so that the direction of flow follows the markings on the device. Note that some chromatographs have default reverse-flow functions built into their software that can cause the flow direction to be reversed without warning. Make sure this function is disabled before conducting any experiments.

The Primary Amine Monolith is delivered in 20% ethanol. It is recommended that it be sanitized and regenerated as described below prior to actual use. It is also recommended that a run be performed without sample to provide a baseline against which to compare experimental results. Some buffer components absorb UV and some transitions between buffers may create refractive index artefacts that can confuse interpretation of experimental results.

Sample and preparation: The Primary Amine Monolith can be used to process in vitro transcription mixtures, including after digestion with DNAse and/or proteinase K, as well as ssRNA resuspended from salt or organic solvent precipitates, or partially purified ssRNA from other purification methods. Samples that contain divalent metal cations should be treated with a chelating agent at about 10 times the estimated concentration of the metal ions. Particulates must be removed by centrifugation or filtration (0.45 µm) in advance of injection. Sample pH should be between pH 6.0 and 8.0. Salt content is not a consideration.

Buffer A: Equilibration buffer/gradient start buffer. 20 mM Tris, 20 mM bis-tris-propane, 20 mM glycine, 50 mM NaCl, pH 8.0.

Buffer B. High-salt wash buffer. 50 mM Tris, 3.0 M guanidine-HCl, 20 mM EDTA, pH 8.0.

Buffer C. Gradient endpoint buffer. 20 mM Tris, 20 mM bis-tris-propane, 20 mM glycine, 50 mM NaCl, pH 11.0.

Buffer D. Cleaning/sanitization buffer. 2 M NaCl, 1 M NaOH.

Buffer E. Regeneration buffer. 3.0 M ammonium acetate.

Equilibrate column with buffer A: Pump equilibration buffer through the column until output pH and conductivity are the same as the input buffer. Flow rate: 10 column volumes (CV)/min.

Inject sample. Observe operating pressure during application of large volume samples, especially with crude samples like in vitro transcription mixtures. Reduce flow rate if necessary to maintain operating pressure within acceptable limits.

Wash1 with buffer A: 5-10 CV of equilibration buffer. It is not necessary to wait for UV signal to return fully to baseline because trailing contaminants will be eliminated by the subsequent high-salt wash step.

Wash2 with buffer B: 10-20 CV of equilibration buffer. Note that guanidine absorbs UV so there will be an immediate peak. DNA and dsRNA typically elute as a fairly sharp peak approaching the crest of the peak. Continue washing until the guanidine peak reaches a level plateau.

Wash3 with buffer A: 10-20 CV of equilibration buffer or until UV returns to baseline.

Elution gradient to buffer C: 50-100 CV linear gradient to 100% gradient endpoint buffer, then hold at 100% for 10 CV. Neutralize fractions immediately after elution.

Clean/sanitize with buffer D. Treatment with 10-20 CV of sanitization buffer is recommended after every run since it will reveal if a significant amount of material remains bound to the column at the end of the pH gradient. The contents of the sanitization step may be collected and neutralized upon elution for further analysis. If the column is loaded with in vitro transcription mixture, it may be necessary to extend duration of the sanitization step to 1 hour. In cases of extreme fouling, it may be necessary to extend the duration of sanitization to 16-24 hours. Maintaining minimal flow rate during sanitization tends to produce better results since it continually replenishes OH ions and washes foulants out of the column instead of merely hydrolyzing them in place.

Regenerate the column: Flush NaOH from the column with 20 CV buffer A or water then wash with 20 CV of buffer E. This is to displace hydroxide counterions from the surface of the monolith since they will otherwise retard equilibration of the column and may create pH artifacts during elution.

Storage: After sanitization and flushing the column with buffer A or water, store in 20% ethanol.

Figure 8:
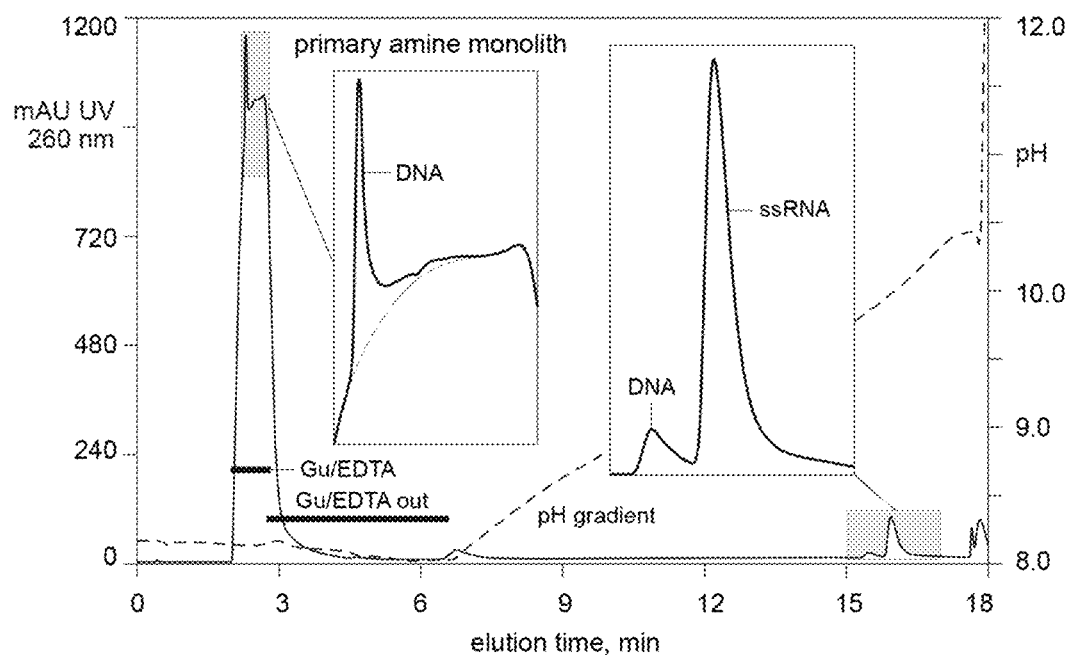
FIG. 8 depicts separation of dsRNA from ssRNA with a primary amino solid phase, with DNA eliminated by a combined chelator-chaotrope step in advance of eluting ssRNA by means of a pH gradient at ambient temperature.

A representative chromatogram is illustrated in FIG. 8.

Variations, Optimization, and Trouble-Shooting

Use the chromatogram as a guide for optimizing the duration of individual steps. Extensive variation of the high-salt wash is possible, for example using different chaotropic salts at concentrations up to full saturation and different concentrations of chelating agents. The concentrations given in the protocol are intended as starting points. If lower concentrations provide equivalent purity, the lesser amounts will reduce material expense and simplify buffer preparation.

Non-chaotropic salts can be substituted for chaotropic salts but exercise caution when applying high concentrations of salts that precipitate RNA. These include sodium chloride, potassium chloride, lithium chloride, among others. Preliminary experimental results indicate that washing with 1 M sodium chloride clears most of the dsRNA and DNA but may also require an extended wash to restore UV absorbance to baseline (FIG. 1).

A workflow simplification can be performed in which guanidine and EDTA are added directly to the sample, and the column is equilibrated to the high-salt wash buffer. Follow the sample load with a first-wash using high-salt buffer, then a second-wash using buffer A from above, then elute. Note that this approach may also support higher ssRNA binding capacity since it will prevent dsRNA and DNA from competing for binding surface area. Column fouling may also be reduced by this approach.

The high-salt wash step can be omitted entirely. This may be preferred for analytical characterization of samples where the objective is to determine the relative amounts of dsRNA and ssRNA, or DNA and ssRNA. The method generally does not discriminate between dsRNA and DNA.

Figure 6:
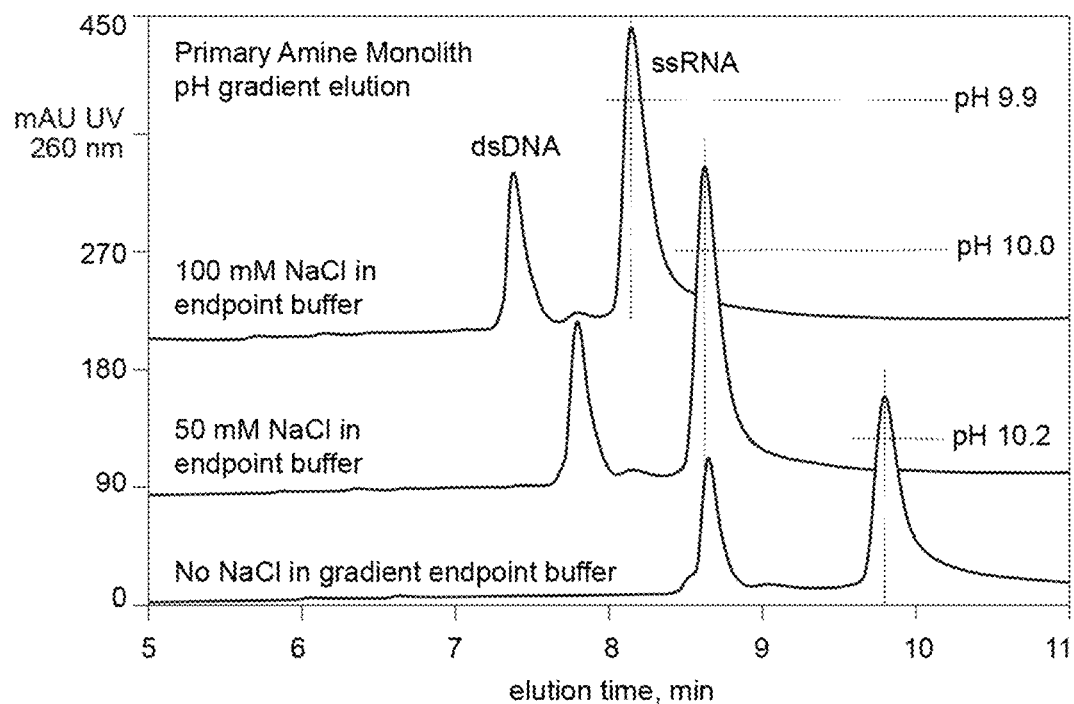
FIG. 6 depicts the effect on separation of DNA and ssRNA of combining salt with pH gradient elution at ambient temperature.

Omission of salt from the pH gradient will increase the separation of dsRNA and ssRNA but doing so may depress recovery and will also increase the pH at which elution occurs. The use of salts that precipitate RNA is acceptable as long as their concentration is maintained well below precipitating levels (FIG. 6). Salts that promote solubility of RNA, like chaotropes, may also be used during pH elution but consider that they may interfere with follow-on purification methods.

Operating temperature may be elevated during the pH gradient, with the effect of causing solutes to elute earlier. Uncontrolled operating temperature may compromise reproducibility.

The linear pH gradient can be converted to a step gradient format. In some cases, such as where CIMmultus dsX-beta is combined with an orthogonal purification method, it may be practical to elute the ssRNA with a single pH step.

Indications of inadequate cleaning may include a gradual increase of operating pressure over a series of runs, a selectivity shift where a given species elutes earlier or later than in a previous run, and/or the appearance of ghost peaks where peaks appear during elution despite no sample having been injected.

The invention is further explained by the following non-limiting examples.

EXAMPLES

Example 1

Separation of dsRNA from ssRNA with a primary amino solid phase, with dsRNA eliminated by a salt step in advance of eluting ssRNA by means of a pH gradient at ambient temperature.

A sample containing a dsRNA ladder dsRNA molecules ranging from 21 b to 500 b and a ssRNA ladder with ssRNA molecules ranging in size from 200 b to 6000 b was applied to a primary amine solid phase in the form of a monolithic chromatography device. The primary amine monolith was equilibrated with 20 mM Tris, 20 mM bis-tris-propane, 20 mM glycine, pH 8.0. The sample was applied, and a wash was applied to displace unbound materials from the channels within the monolith. A wash step with 20 mM bis-tris-propane, 20 mM glycine, 1 M NaCl, pH 8.0 was then applied, followed by another wash step to remove the NaCl. The monolith was then eluted with a linear gradient to 20 mM Tris, 20 mM bis-tris-propane, 20 mM glycine, pH 11.0. As shown in FIG. 1, all of the dsRNA species eluted in the NaCl step while the ssRNA remained bound and eluted later in the pH gradient. No apparent size separation is observed among species in the dsRNA ladder but clear separation is observed among species in the ssRNA ladder.

Example 2

Separation of dsRNA from ssRNA with a primary amine solid phase, with dsRNA eliminated by a wash step containing 6 M guanidine-HCl and 20 mM EDTA in advance of eluting ssRNA by means of a pH gradient at ambient temperature.

Figure 2:
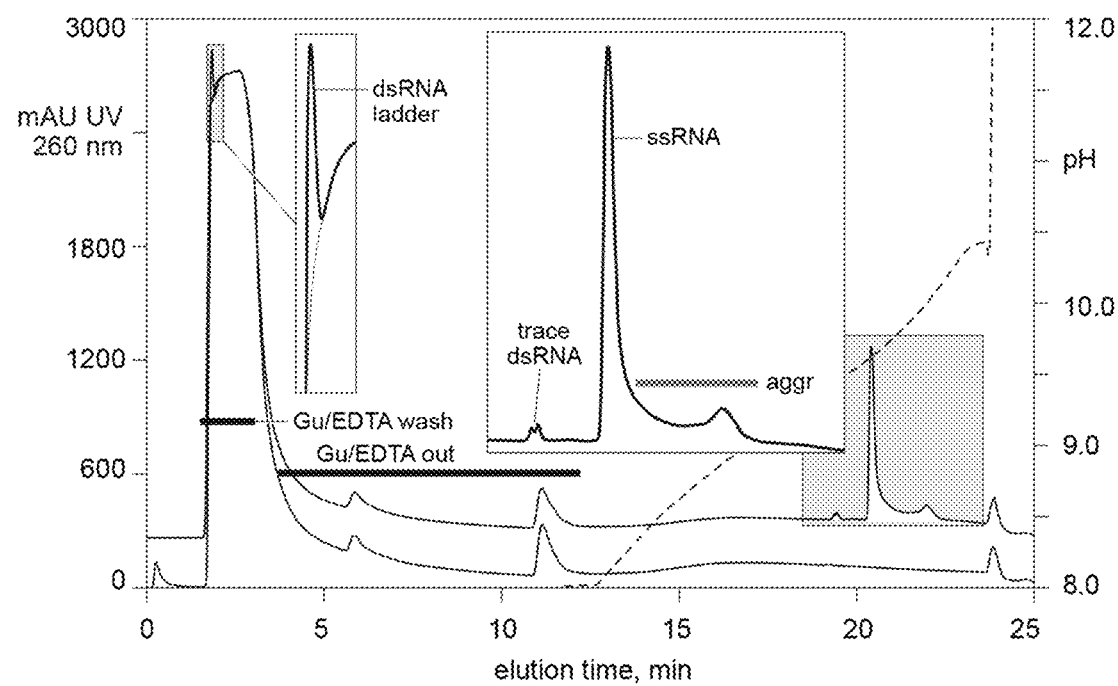
FIG. 2 depicts separation of dsRNA from ssRNA with a primary amino solid phase, with dsRNA eliminated by a 6 M guanidine step in advance of eluting ssRNA by means of a pH gradient at ambient temperature.

A sample containing a dsRNA ladder with dsRNA molecules ranging from 21 b to 500 b and ssRNA with a size of 5000 b was applied to a primary amine solid phase in the form of a monolithic chromatography device. The primary amine monolith was equilibrated with 20 mM Tris, 20 mM bis-tris-propane, 20 mM glycine, pH 8.0. The sample was applied, and a wash was applied to displace unbound materials from the channels within the monolith. A wash step with 20 mM bis-tris-propane, 20 mM glycine, 6 M guanidine, 20 mM EDTA, pH 8.0 was then applied, followed by another wash step to remove the guanidine and EDTA. The monolith was then eluted with a linear gradient to 20 mM Tris, 20 mM bis-tris-propane, 20 mM glycine, pH 11.0. As shown in FIG. 2, all of the dsRNA species eluted in the salt step while the ssRNA remained bound and eluted later in the pH gradient.

Example 3

Failure of a pH gradient to elute ssRNA from a strong anion exchanger and a weak anion exchanger.

Figure 3:
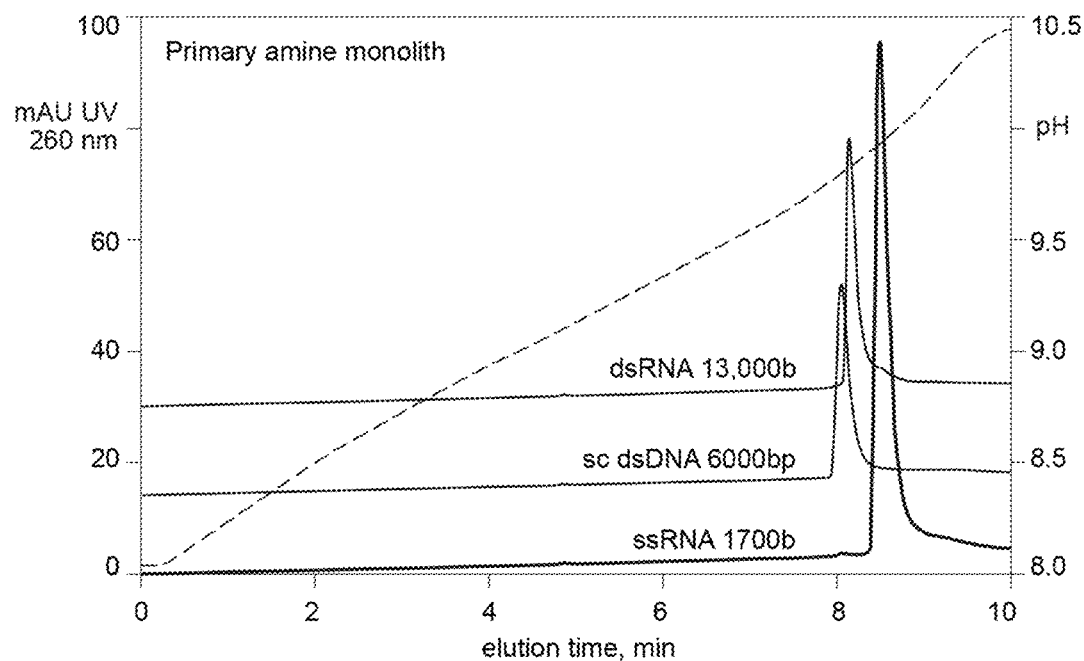
FIG. 3 depicts the failure of ssRNA to elute in a pH gradient at ambient temperature from a strong anion exchanger and from a weak anion exchanger.

Behavior of ssRNA in a pH gradient was characterized using a strong (quaternary amine, QA) anion exchanger and a weak (tertiary amine, DEAE) anion exchanger as experimental controls against which to compare the performance of pH gradient elution on a primary amino solid phase. Both anion exchangers were in the physical forms of monolithic devices with a volume of 1 mL. The columns were equilibrated with 20 mM Tris, 20 mM bis-tris-propane, 20 mM glycine, pH 8.0. A sample containing ssRNA of about 5000 nucleotide bases (5000 b) was injected and the column was washed with equilibration buffer to displace unbound materials. The columns were then eluted with a linear gradient to 20 mM Tris, 20 mM bis-tris-propane, 20 mM glycine, pH 11.0. FIG. 3 shows that ssRNA did not elute within the pH gradient on either the strong anion exchanger or the weak anion exchanger and was removed only by cleaning the columns with 1 M NaOH.

Example 4

Separation of plasmid DNA from ssRNA with a primary amino solid phase by means of a pH gradient at ambient temperature.

Figure 4:
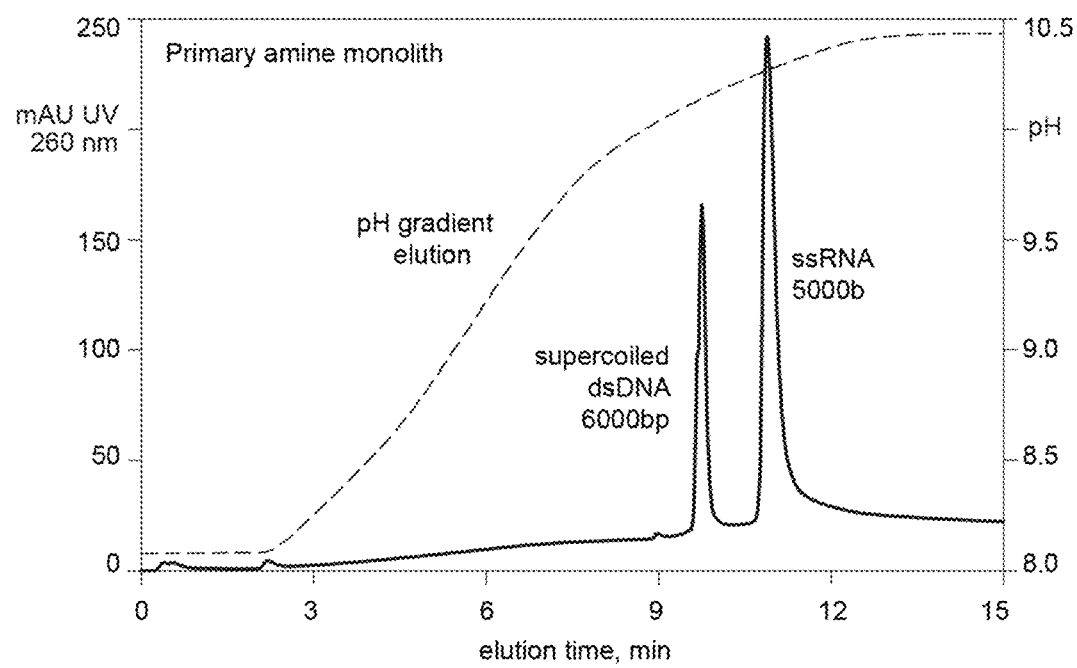
FIG. 4 depicts separation of plasmid DNA from ssRNA with a primary amino solid phase by means of a pH gradient at ambient temperature.

A sample containing a supercoiled dsDNA plasmid with a size of about 6000 base pairs and ssRNA with a size of about 5000 bases was applied to a primary amine solid phase in the form of a monolithic chromatography device. The primary amine monolith was equilibrated with 20 mM Tris, 20 mM bis-tris-propane, 20 mM glycine, pH 8.0. The sample was applied, and a wash was applied to displace unbound materials from the channels within the monolith. The monolith was then eluted with a linear gradient to 20 mM Tris, 20 mM bis-tris-propane, 20 mM glycine, pH 11.0. As shown in FIG. 4, the DNA plasmid eluted first, well separated from the later eluting ssRNA.

Example 5

Separation of plasmid DNA from ssRNA with a primary amino solid phase with DNA eliminated by a salt step in advance of eluting ssRNA by means of a pH gradient at ambient temperature.

Figure 5:
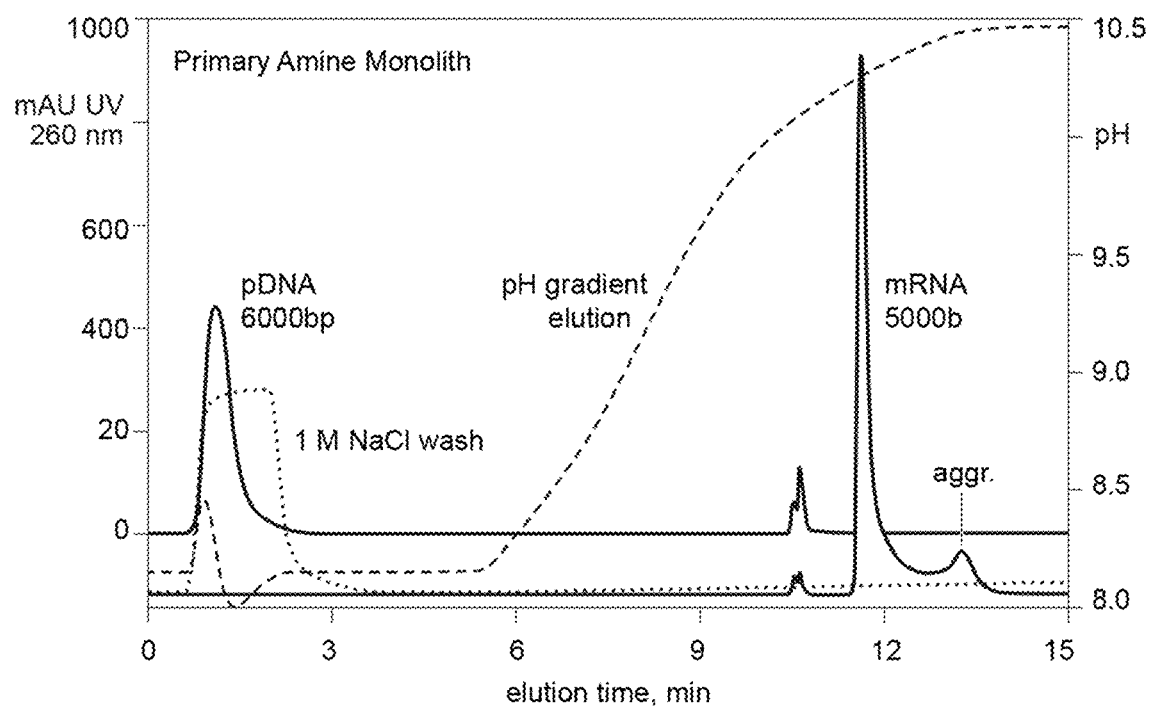
FIG. 5 depicts separation of plasmid DNA from ssRNA with a primary amino solid phase, with DNA eliminated by a salt step in advance of eluting ssRNA by means of a pH gradient at ambient temperature.

A sample containing a supercoiled dsDNA plasmid with a size of about 6000 base pairs and ssRNA with a size of about 5000 bases was applied to a primary amine solid phase in the form of a monolithic chromatography device. The primary amine monolith was equilibrated with 20 mM Tris, 20 mM bis-tris-propane, 20 mM glycine, pH 8.0. The sample was applied, and a wash was applied to displace unbound materials from the channels within the monolith. A wash step with 20 mM bis-tris-propane, 20 mM glycine, 1 M NaCl, pH 8.0 was then applied, followed by another wash step to remove the NaCl. The monolith was then eluted with a linear gradient to 20 mM Tris, 20 mM bis-tris-propane, 20 mM glycine, pH 11.0. As shown in FIG. 5, the DNA plasmid eluted in the salt step while the ssRNA remained bound and eluted later in the pH gradient.

Example 6

The effect on separation of DNA and ssRNA of combining salt with pH gradient elution at ambient temperature.

A series of separations were performed comparing simple pH gradient elution, with pH gradient elution where the endpoint buffer contained 50 mM NaCl, with pH gradient elution where the endpoint buffer contained 1000 mM NaCl. In each experiment, a sample containing a supercoiled dsDNA plasmid with a size of about 6000 base pairs and ssRNA with a size of about 5000 bases was applied to a primary amine solid phase in the form of a monolithic chromatography device. The primary amine monolith was equilibrated with 100 mM Tris, pH 8.0. The sample was applied, and a wash was applied to displace unbound materials from the channels within the monolith. In the first experiment, the monolith was eluted with a linear gradient to 125 mM glycine, pH 10.5. In the second experiment, the monolith was eluted with a linear gradient to 125 mM glycine, 50 mM NaCl, pH 10.5. In the third experiment, the monolith was eluted with a linear gradient to 125 mM glycine, 100 mM NaCl, pH 10.5. As shown in FIG. 6, the center of the ssRNA peak occurred at pH 10.2 when no sodium chloride was included. With 50 mM sodium chloride in the gradient endpoint buffer, ssRNA eluted at pH 10.0. With 100 mM sodium chloride in the gradient endpoint buffer, ssRNA eluted at pH 9.9. When sodium chloride was maintained at a level concentration of 50 mM across the pH gradient, ssRNA eluted at pH 9.8 (not shown). When sodium chloride was maintained at a level concentration of 100 mM across the pH gradient, ssRNA eluted at pH 9.6 (not shown). Inclusion of sodium chloride caused other effects of interest. The separation between DNA and ssRNA was greatest in the absence of NaCl and larger amounts of NaCl diminished the separation further. However, the recovery of ssRNA was clearly improved in the presence of sodium chloride.

Example 7

Uniformity of response by dsRNA and DNA.

Figure 7:
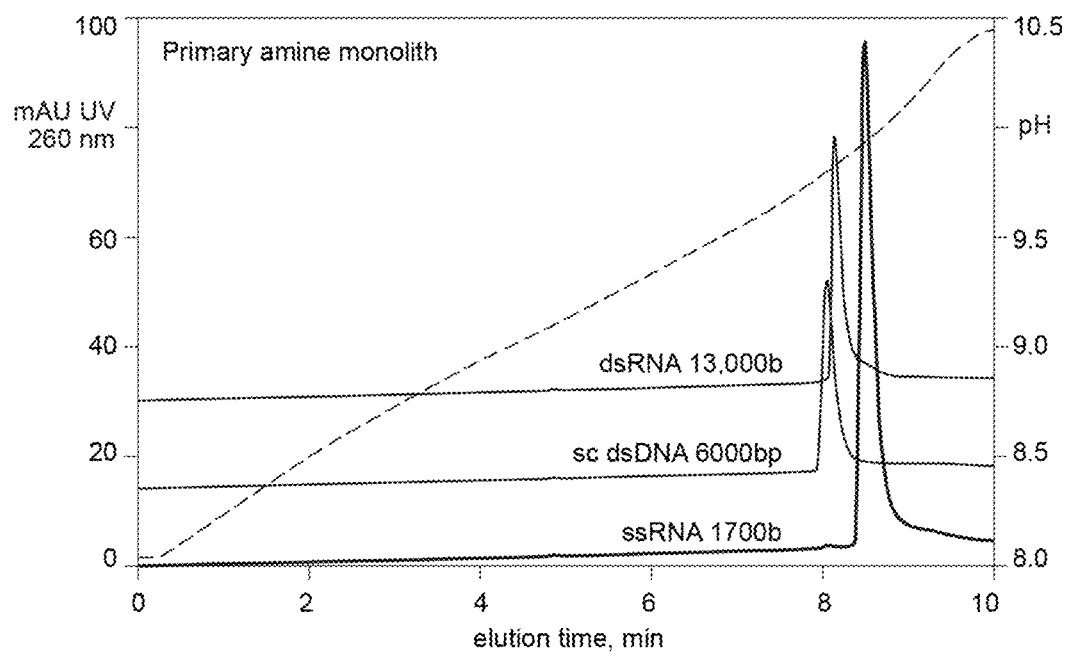
FIG. 7 depicts separation of large DNA and very large dsRNA from small ssRNA on a primary amino solid phase by means of a pH gradient at ambient temperature.

As is apparent among the foregoing experiments, dsRNA and DNA behave similarly, both eliminated by a salt wash, and suggesting that both should be separated from ssRNA within a pH gradient, and also suggesting that DNA can be used as a model for dsRNA behavior to characterize the method of the invention. An experiment was performed to test the ability of the method of the invention in an extreme worst case that would never occur in the course of purifying ssRNA from a representative transcription mixture. The test involved separating a relatively small ssRNA of about 1700 bases from dsRNA with a size of about 13,000 bases, and comparing the elution behavior of 13 kb dsRNA with a DNA plasmid of about 6000 base pairs. A primary amine monolith was equilibrated with 100 mM Tris, pH 8.0. In each experiment, the sample was applied, and a wash was applied to displace unbound materials from the channels within the monolith. The monolith was then eluted with a linear gradient to 125 mM glycine, pH 10.5. As shown in FIG. 7 and consistent with expectations, DNA and very-large dsRNA co-eluted to a large extent with both eluting before the much smaller ssRNA. The degree of separation between ssRNA and the two larger contaminants was reduced compared to other examples but a clear separation was nevertheless apparent. In actual practice, dsRNA in a given in vitro transcription mixture would contain the same number of bases as ssRNA. Comparing with Example 4, showing that ssRNA elutes later in a pH gradient according to its size, this suggests that the invention will provide a good separation between dsRNA and ssRNA, no matter what their size. The point may be moot given that dsRNA can be removed so easily by a salt wash in advance of eluting ssRNA with a pH gradient, but it shows that the invention can achieve effective separation even lacking a salt wash. The results of FIG. 7 are also of note to the extent that they show the invention should work well with ssRNA of at least 15,000 b and likely up to 25,000 b or more.

Example 8

Separation of dsRNA from ssRNA with a primary amine solid phase, with DNA eliminated by a combined chelator-chaotrope step in advance of eluting ssRNA by means of a pH gradient at ambient temperature.

A sample containing a 6000 bp supercoiled dsDNA plasmid and a 5000 b ssRNA with was applied to a primary amine solid phase in the form of a monolithic chromatography device. The primary amine monolith was equilibrated with 20 mM Tris, 20 mM bis-tris-propane, 20 mM glycine, pH 8.0. The sample was applied, and a wash was applied to displace unbound materials from the channels within the monolith. A wash step with 20 mM bis-tris-propane, 20 mM glycine, 1 M guanidine-HCl, 20 mM EDTA, pH 8.0 was then applied, followed by another wash step to remove the guanidine and EDTA. The monolith was then eluted with a linear gradient to 20 mM Tris, 20 mM bis-tris-propane, 20 mM glycine, pH 11.0. FIG. 8 shows that most of the DNA plasmid was eliminated in the guanidine-EDTA (chaotrope-chelator) wash. The remaining bound DNA eluted in advance of ssRNA in the pH gradient.

Comparing FIG. 8 (using 1 M guanidine) to FIG. 5 (using 6 M guanidine), the results suggest that 1 M guanidine-HCl is insufficient to completely dispose of the DNA in advance of eluting the ssRNA. In FIG. 5, the dsRNA peak was concentrated on the leading edge of the 6 M guanidine wash peak. In FIG. 8, DNA begins to elute toward the front of the guanidine wash but clearly later than in FIG. 5 and there is conspicuous tailing. The relative size of the DNA/ssRNA peak eluting immediately in advance of the ssRNA peak further supports the conclusion that 1 M guanidine HCl does not fully dispose of the DNA/dsRNA in advance. Note also however that the ssRNA elutes in a single peak following an advance wash with 1 M guanidine (FIG. 8), versus FIG. 5 (following 6 M guanidine) where an ssRNA peak was observed as expected but it was followed by later eluting materials that were interpreted to represent aggregates. The comparison suggests that it will be valuable as a routine part of process optimization to adjust the chaotrope concentration to provide the best clearance of DNA/sdRNA without altering the behavior of the desired ssRNA.

Example 9

Reduction of ssRNA elution pH by inclusion of multivalent anions.

Figure 9:
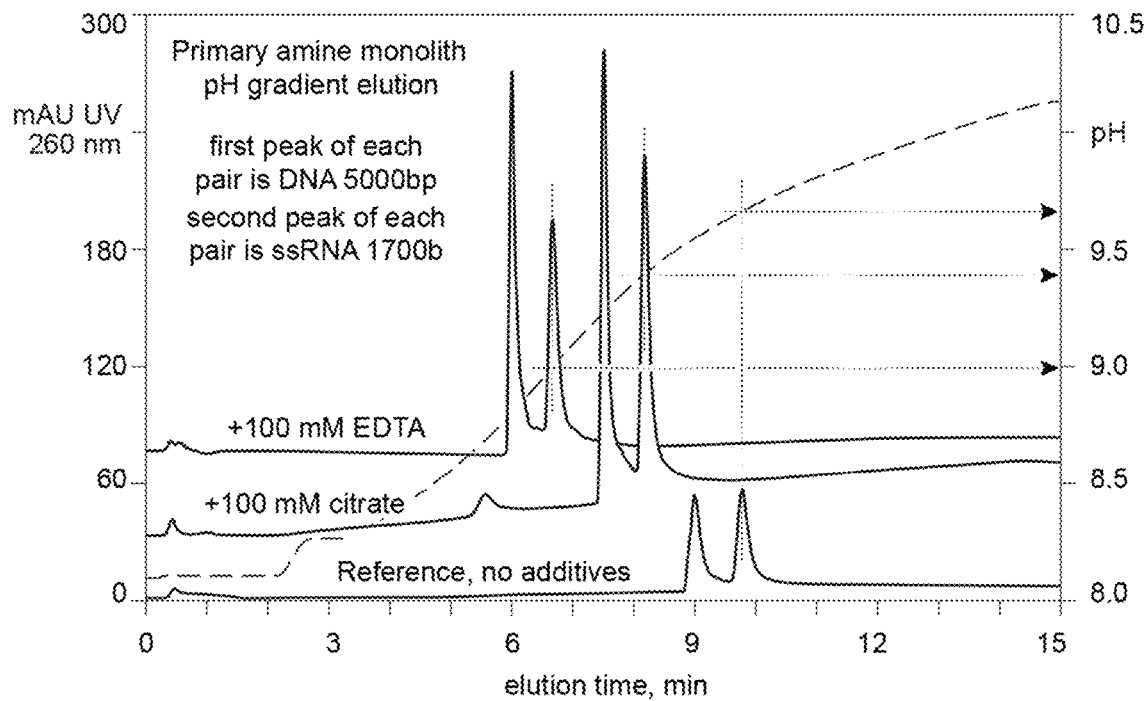
FIG. 9 depicts lowering of the pH at which ssRNA elutes in a pH gradient by inclusion of chelating salts.

A series of experiments was performed in which a mixture of DNA and ssRNA was fractionated in a pH gradient. A primary amine solid phase was equilibrated with 100 mM Tris, pH 8.0. Sample was loaded then washed with equilibration buffer. A linear gradient of 125 device volumes applied to an endpoint buffer of 125 mM glycine, pH 10.5. In a second run, the conditions were repeated except adding 100 mM citrate to the buffers. In a third run, the conditions were repeated except adding 100 mM ethylenediaminetetraacetate (EDTA) to the buffers. As shown in FIG. 9, both additives strongly reduced the pH at which both DNA and ssRNA eluted, with the strongest pH reduction observed with EDTA. The degree of pH reduction of both was also greater than achieved with 100 mM sodium chloride (FIG. 6). A point in common with the sodium chloride results was that the presence of salt increased the recovery of DNA and ssRNA in the elution gradient. Another point of similarity was that elution with either sodium chloride, citrate, or EDTA failed to elute ssRNA at pH values of pH 8.0 or less.

Example 10

Purification of ssRNA with high-salt wash in advance of elution with a pH gradient in the presence of salts.

A primary amine solid phase in the form of a chromatography device such as a monolith is equilibrated to 50 mM Tris, 20 mM EDTA, 2 M guanidine isothiocyanate, 8.0±0.5. The UV monitor is zeroed. EDTA and guanidine isothiocyanate are added to the sample and the sample pH is adjusted to pH 8.0±0.5. The sample is filtered if necessary to remove turbidity. The sample is applied to the primary amine monolith and the monolith is washed with equilibration buffer until the baseline returns to zero. Sample application and washing in a strong chelating-chaotrope solution is intended to prevent binding of and/or remove dsRNA, DNA, and proteins to trace levels. The monolith is then washed for at least 10 device volumes of 50 mM Tris, 5 mM EDTA, 100 mM guanidine isothiocyanate, pH 8.0±0.5. The ssRNA is then eluted with a linear gradient to 65 mM glycine, 5 mM EDTA, 100 mM guanidine isothiocyanate, pH 10.5±0.5. The presence of a chelating agent is maintained throughout the method to prevent adverse effects due to the potential presence of multivalent metal cations. 100 mM guanidine isothiocyanate is substituted for the 100 mM sodium chloride described in Example 6 or the 100 mM citrate or 100 mM EDTA described in Example 9 to avoid reducing the solubility of ssRNA. In a parallel experiment, the concentration of guanidine isothiocyanate is increased with the intent of further reducing the pH at which the ssRNA elutes, if desired. In a parallel experiment, the chaotropic salt guanidine thiocyanate is replaced with a different salt, if desired. In a parallel experiment, the species and concentration of the chelating agent is altered, if desired.

Example 11

Elution of in vitro transcription mixture from a primary amine solid phase with a combined pH-salt gradient.

Figure 10:
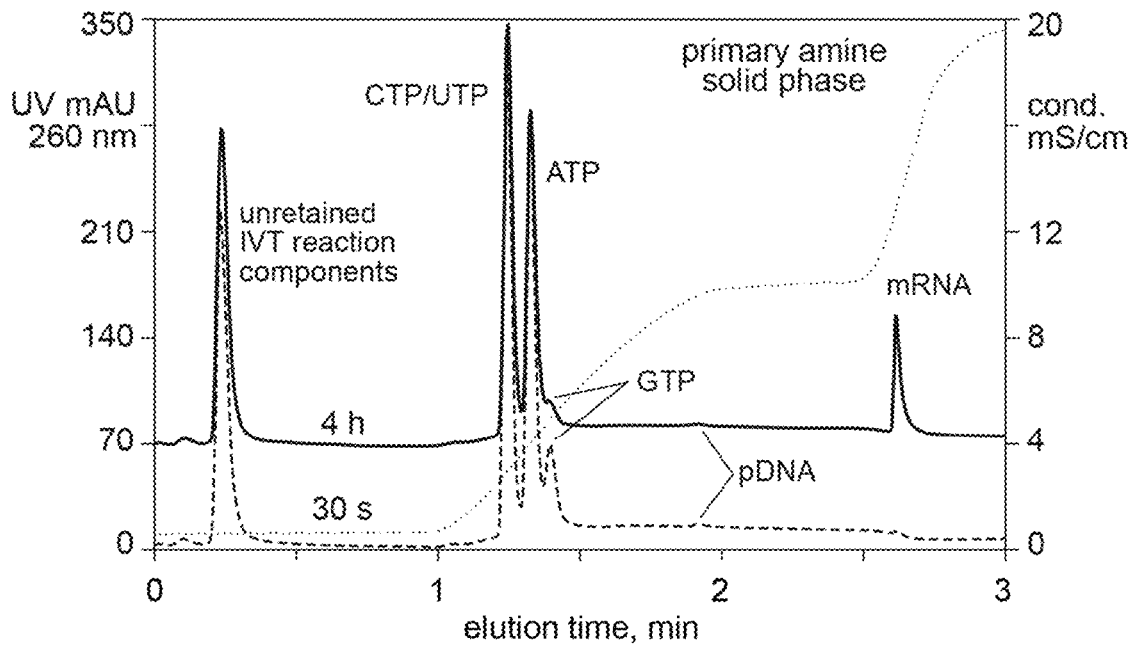
FIG. 10 depicts monitoring of an in vitro transcription reaction at different time points with a primary amine solid phase, eluted with a pH gradient in the presence of salt.

The following buffers were prepared: Buffer A, containing 50 mM Hepes, pH 7.0; Buffer B, containing 50 mM Hepes, 200 mM sodium pyrophosphate, pH 8.5; Buffer C, containing 100 mM sodium hydroxide, 2.0 M sodium chloride; and Buffer D, containing 1.5 M Hepes, pH 7.0. A primary amine monolith with 2 μm channels and a bed volume of 100 μL stored in 20% ethanol was washed with 50 CV water at a flow rate of 2 mL/min (20 CV/min). The column was equilibrated with Buffer A and a 25 μL sample of in vitro transcription mixture taken at 30 s from the start of the reaction was injected. The column was washed with 20 CV of buffer A then a 40 CV linear gradient to 20% buffer B was applied, followed by a 10 CV gradient hold at 20% buffer B. This segment eluted nucleotides and double-stranded species including the DNA plasmid. A 10 CV linear gradient to 50% buffer B was applied to elute mRNA, followed by a gradient hold at 50% B. An additional 10 CV linear gradient to 100% B was applied, followed by a 10 CV gradient hold. The column was cleaned with buffer C, then restored to pH 7 with buffer D. The column was re-equilibrated and injected with a sample taken 4 h after initiation of in vitro transcription. Elution was performed as for the previous sample. After completion of the run, the column was washed with 20% ethanol and stored in that solution. All chromatography steps were performed at ambient temperature. The elution profiles are shown in FIG. 10. The profile corresponding to the sample taken at 30 s is shown by the long-dash line. The profile corresponding to the sample taken at 4 h is shown by the solid line. The short-dash line indicates conductivity. As expected, levels of constituent nucleotides such as CTP, UTP, ATP, and GTP were reduced to lower levels over the course of in vitro transcription, reflecting their incorporation into the newly synthesized mRNA.

REFERENCES

All references cited herein are incorporated by reference to the full extent to which the incorporation is not inconsistent with the express teachings herein.

[1] M Baiersdorfer, G Boros, H Murumatsu, A Mahini, I Vlatkovic, U Sahin, K Kariko, A fascile method for the removal of dsRNA contaminant from in vitro-transcribed mRNA, Molecular therapy: nucleic acids, 15 (2019)

[2] S. Urayama, Y. Yoshida-Takashima, M. Yoshida, Y. Tomaru, H. Moriyama, K. Takai, T. Nunoura, A New Fractionation and Recovery Method of Viral Genomes Based on Nucleic Acid Composition and Structure Using Tandem Column Chromatography. Microbes Environ. 30, (2015) 199-203.

[3] R. Franklin, Purification and properties of the replicative intermediate of the RNA bacteriophage R17. Proc. Natl. Acad. Sci. USA 55, (1966) 1504-1511.

[4] A Nwokeoji, AW Kung, P Kilby, D Portwood, M Dickman, Purification and characterization of dsRNA using ion pair reverse phase chromatography and mass spectrometry, J. Chromatography A 1484 (2017) 14-25.

[5] A Nwokeoji, M Earll, P Kilby, D. Portwood, M. Dickman, High resolution fingerprinting of double-stranded RNA using ion-pair reversed phase chromatography, J. Chromatography B 1104 (2019) 212-219.

[6] K Kariko, H Muramatsu, J Ludwig, D. Weismann, Generating the optimal mRNA for therapy: HPLC purification eliminates immune activation and improves translation of nucleoside-modified, protein-encoding mRNA, Nucleic acid research, 39 (2011) e142.

[7] D. Weismann, N. Pardi, H Murumatsu, K Kariko, HPLC purification of in vitro transcribed long RNA, Methods Molecular Biology, 969 (2013) 43-54.

[8] A Romanovskaya, L P Sarin, D H Bramford, M M Poranen, High-throughput purification of double-stranded R.N.A. molecules using convective interaction media monolithic anion exchange columns, J. Chromatography A, 1278 (2013) 54-60.

[9] WO 2014/144767 A1

The invention claimed is:

1. A method of single-stranded RNA purification comprising the steps
    applying a sample comprising single-stranded RNA to a solid phase having a surface bearing amino groups, wherein the amino groups comprise at least 50% primary amino groups, at a first pH value in a range sufficient to bind the single-stranded RNA,
    eluting the single stranded RNA from the surface of the solid phase by exposing the surface of the solid phase to an ascending pH gradient having a range of pH values that are higher than the first pH value, wherein the single-stranded RNA is collected as a purified fraction.

2. The method of claim 1 further comprising washing of the solid phase one or more times after applying the sample and prior to eluting of the single-stranded RNA, wherein at least one step of washing of the solid phase is provided with a washing buffer having a first ionic strength, wherein the elution buffer has a second ionic strength, and wherein the first ionic strength is higher than the second ionic strength.

3. The method of claim 2 wherein after the at least one step of washing of the solid phase with a washing buffer, the method further comprises at least one step of washing to reduce the ionic strength below the first ionic strength.

4. The method of claim 1 further comprising washing the solid phase one or more times after applying the sample and prior to eluting of the single-stranded RNA, wherein at least one step of washing is provided with a washing buffer having a pH that is higher than the first pH value and which keeps single-stranded RNA adsorbed to the solid phase and desorbs remaining double-stranded RNA.

5. The method of claim 2 wherein the first ionic strength from 0.5 M to 12 M higher than the second ionic strength.

6. The method of claim 2 wherein the first ionic strength is adjusted with a concentration of a chaotropic salt.

7. The method of claim 1 wherein eluting of the single-stranded RNA from the surface of the solid phase occurs by means of an elution buffer having a pH in a pH range of pH 7.5 to pH 12.0.

8. The method of claim 1 wherein the first pH value is less than about pH 8.5.

9. The method of claim 1 wherein the sample comprises an aqueous mixture and wherein a chelating agent is present in the aqueous mixture, in an environment of the surface of the solid phase prior to the contacting of the aqueous mixture, in a buffer for eluting the single-stranded RNA from the surface of the solid phase and/or in a separate buffer employed between the steps of applying the sample to the solid phase and/or eluting the single-stranded RNA from the surface of the solid phase.

10. The method of claim 9 wherein the chelating agents are independently selected from the group consisting of ethylenediaminetetraacetic acid (EDTA), a salt of citric acid, phosphoric acid, or ethylene glycol-bis (2-aminoethylether)-N,N,N',N'-tetraacetic acid (EGTA), tris (2-aminoethyl)-amine (TREN), and a mixture thereof.

11. The method of claim 1 wherein the single-stranded RNA is of size in the range of 1000 bases to 25,000 bases.

12. The method of claim 2 wherein the first ionic strength from 1.0 M to 10 M higher than the second ionic strength.

13. The method of claim 2 wherein the first ionic strength from 2.0 M to 8.0 M higher than the second ionic strength.

14. The method of claim 2 wherein the first ionic strength from 4.0 M to 6.0 M higher than the second ionic strength.

15. The method of claim 6 wherein the chaotropic salt is selected from the group consisting of guanidinium salts, thiocyanates, perchlorates and combinations thereof.

16. The method of claim 7 wherein eluting of the single-stranded RNA from the surface of the solid phase occurs by means of an elution buffer having a pH in a pH range selected from the group of ranges consisting of pH 8.0 to pH 11.5, pH 8.5 to pH 11, and pH 9.0 to pH 10.5.

17. The method of claim 1 wherein the surface of the solid phase consists essentially of primary amines.

18. The method of claim 1 wherein the sample comprises a mixture of double-stranded RNA and single-stranded RNA and wherein the single-stranded RNA selectively adsorbs to the solid phase during the applying step.

19. The method of claim 2 wherein the washing buffer has a pH that is higher than the first pH value and which keeps single-stranded RNA adsorbed to the solid phase and desorbs double-stranded RNA.

20. The method of claim 2 wherein the washing buffer has a pH that is the same as the first pH value.

* * * * *